(12) United States Patent
Toumbas et al.

(10) Patent No.: US 8,735,056 B2
(45) Date of Patent: May 27, 2014

(54) INSTRUMENT AND METHOD FOR OPTICAL PARTICLE SENSING

(75) Inventors: Paul Toumbas, New Port Richey, FL (US); Don Gabriel, Carrboro, NC (US)

(73) Assignee: Invitrox, Inc., Durham, NC (US)

( * ) Notice: Subject to any disclaimer, the term of this patent is extended or adjusted under 35 U.S.C. 154(b) by 0 days.

(21) Appl. No.: 13/322,132

(22) PCT Filed: May 20, 2010

(86) PCT No.: PCT/US2010/035621
§ 371 (c)(1),
(2), (4) Date: Feb. 6, 2012

(87) PCT Pub. No.: WO2010/138391
PCT Pub. Date: Dec. 2, 2010

(65) Prior Publication Data
US 2012/0135405 A1    May 31, 2012

Related U.S. Application Data

(60) Provisional application No. 61/181,182, filed on May 26, 2009.

(51) Int. Cl.
*C12Q 1/68* (2006.01)
*G01N 21/47* (2006.01)
*C07H 21/04* (2006.01)

(52) U.S. Cl.
USPC .......... 435/4; 435/6.1; 435/288.1; 422/82.05; 536/23.1

(58) Field of Classification Search
None
See application file for complete search history.

(56) References Cited

U.S. PATENT DOCUMENTS

| | | | |
|---|---|---|---|
| 6,104,490 A * | 8/2000 | Trainer | 356/336 |
| 6,228,652 B1 * | 5/2001 | Rodriguez et al. | 436/63 |
| 6,525,823 B1 | 2/2003 | Dogariu et al. | |
| 6,710,879 B1 | 3/2004 | Hansen et al. | |
| 6,794,671 B2 * | 9/2004 | Nicoli et al. | 250/574 |
| 2004/0011975 A1 * | 1/2004 | Nicoli et al. | 250/574 |
| 2005/0250095 A1 | 11/2005 | Gabriel | |

FOREIGN PATENT DOCUMENTS

WO    2006055562 A1    5/2006

* cited by examiner

*Primary Examiner* — Betty Forman
(74) *Attorney, Agent, or Firm* — Hultquist, PLLC; Steven J. Hultquist; David Bradin

(57) ABSTRACT

A new device capable of measuring the number of particles present in a colloidal suspension is disclosed, which includes a forward scatter detector, an extinction detector, a laser beam, a cylindrical lens with which to create a plane of light through which particles can pass, and the various pumps and tubing needed to pass the colloidal suspension through the plane of light. The device is particularly designed for measuring particles which have different refractive indices, and which are in the size range of between about 0.7 to 2 microns. The device can determine the presence or absence of biological particles of interest in a given sample, by incubating a sample with a given ratio of active particles and marker particles, and determining whether the ratio of active particles and marker particles has changed. Additional binding and/or non-binding particles can also be present, and kits including the particles are also disclosed.

23 Claims, 13 Drawing Sheets

Electro-Optical subsystem, showing light path, and electrical signal path.

1a. Linear Scale.    1b. Log Scale.

Figure 1. Mie Scattering Intensity from a 2μm Diameter Latex Sphere in 25°C Water. Incident beam from the left at 660 nm wavelength, Incident Intensity 1W/m$^2$, plane wave, unpolarized. 1a.) Linear Scale: Max = $2.10 \times 10^{-10}$ Watts, Min = 0 Watts. 1b.) Log Scale Max = $2.10 \times 10^{-10}$ Watts, Min = $2.10 \times 10^{-18}$ Watts.

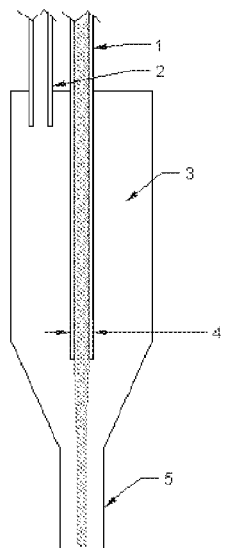
Figure 10.
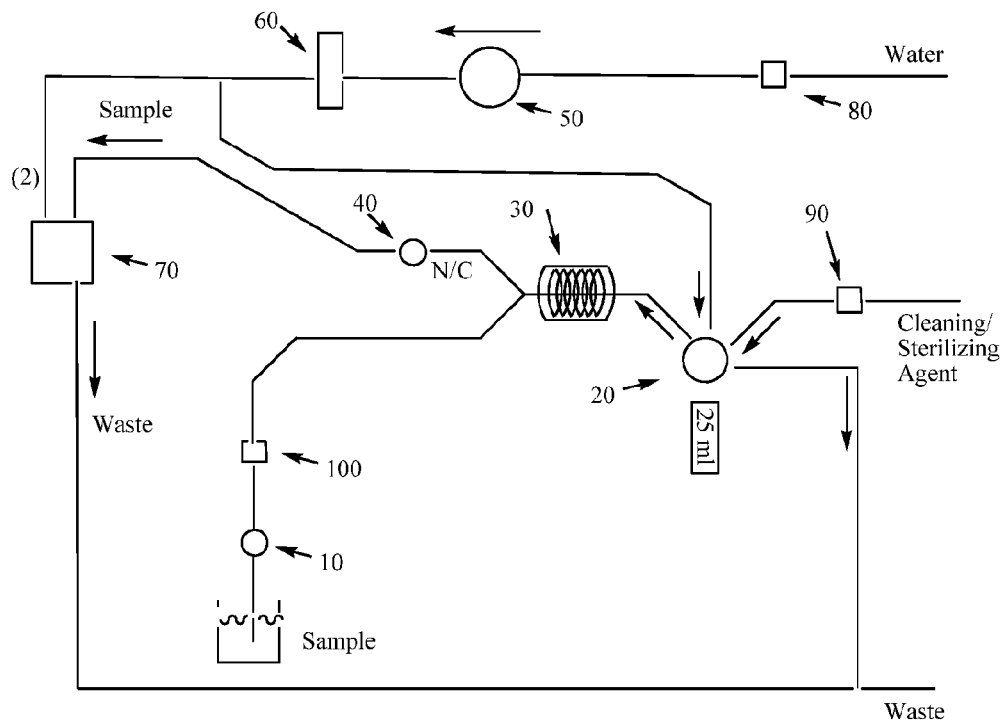
Figure 11. Fluid connections diagram, showing pumps, valves, tubing, storage loop, and flow cell.

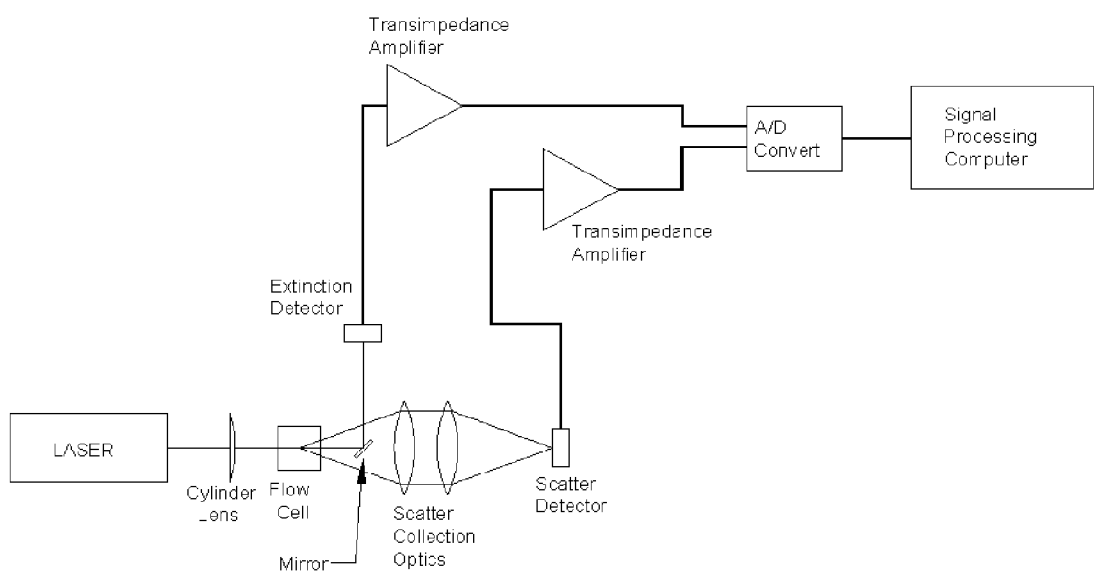
Figure 12. Electro-Optical subsystem, showing light path, and electrical signal path.

INSTRUMENT AND METHOD FOR OPTICAL PARTICLE SENSING

CROSS-REFERENCE TO RELATED APPLICATIONS

This application is a U.S. national phase application under the provisions of 35 U.S.C. §371 of International Patent Application No. PCT/US2010/035621 filed May 20, 2010, which in turn claims priority of U.S. Provisional Patent Application No. 61/181,182 filed May 26, 2009. The disclosures of such international patent application and U.S. priority patent application are hereby incorporated herein by reference in their respective entireties, for all purposes.

FIELD OF THE INVENTION

The invention relates generally to optical sensing of particles suspended in a liquid medium, and, more particularly, to optical sensing of particles to determine particle size, particle number, and/or other properties of the particles. The methods are useful in a variety of biological applications, for example, screening and optimizing drug candidates, evaluating the efficacy and dosage levels of such drugs, developing approaches for personalized medicine, and detecting active disease states.

BACKGROUND OF THE INVENTION

It is often essential to characterize particles by their size, as well as their ability to bind to other particles or molecules. When the particles are biological particles, the information gained about their ability to bind, or not to bind, to certain particles or molecules can provide useful information. Additionally, it is useful in certain diagnostic applications to detect known changes of the surface of a biological particle. Accordingly, it can be desirable to detect the surface chemistry and monitor changes to the surface chemistry in an efficient and accurate manner.

"Electrophoretic Quasi-Elastic Light Scattering" (EQELS) is one method for characterizing biological particles. This method uses electrophoresis that is dependent on the particle's surface charge density to identify and characterize suspended biological particles. EQELS uses cells placed in an electric field, where the surface charge of the particle will determine how that particle moves in the electric field. Monitoring the electrophoretic mobility of the cells provides information useful in distinguishing among different particles in the field. One can screen and optimize drug candidates which interact with the biological particles by comparing the spectra of the particles alone, or particles bound to the drug candidates.

Coulter counters can also be used to characterize biological particles. These devices are used primarily to count and size cells and other biological particles. The Coulter Counter works by drawing fluid containing the biological particle through a small opening located within a current between two electrodes, and detecting the change in electric conductance. As the fluid is drawn through the opening, the biological particles flow through the current and measurably disturb a portion of the current. The measurable displacement is translated to a pulse that is digitally processed by the Coulter Counter and translated to allow one to characterize the size and number of biological particles in the fluid.

Flow cytometry can also be used to characterize biological particles. Flow cytometry uses a beam of light, such as a laser, trained on a fluid to characterize, count and optionally sort particles in the fluid. The fluid is focused into a stream, and detectors near to the intersection of the light and the fluid stream determine light scatter—both forward and side. Additionally, one or more fluorescent detectors may be present to detect fluorescent or fluorescently-tagged particles. One can determine various physical and chemical characteristics of each individual particle by analyzing the detected pattern.

These methods are useful in detecting and characterizing microparticles, including determining the number of particles, number density within a fluid medium, size, and surface characteristics of the particle, confirming binding, or lack thereof, and the like. The particles are generally in the size of between 0.1 µm and 50 µm. However, each of these methods has various limitations, including the speed in which the assays can be performed, the size of particles that can be measured, and the like.

There remains a need for additional devices and processes for characterizing particles, including biological particles, which can detect particles with accuracy, quantify the particles and/or determine whether one or more of the particles bind to other particles or molecules. The present invention provides such devices and processes.

SUMMARY OF THE INVENTION

In one embodiment, the present invention is directed to a new device capable of measuring particles present in a colloidal suspension. The device includes a forward scatter detector, an extinction detector, a laser beam, a cylindrical lens with which to create a plane of light through which particles can pass, and the various pumps and tubing needed to pass the colloidal through the plane of light.

The device can measure particles over a wide range of particle sizes, but is particularly useful for measuring particles in the size range of between about 0.5 to 100 microns, preferably between about 0.7 to 2 microns. In this particular size range, particles with different refractive indices (such as biological cells, with a refractive index of around 1.39 and latex particles, with a refractive index of around 1.59) are easily distinguished. The device offers various advantages over a conventional flow cytometer.

In another embodiment, the present invention is directed to new methods for determining the presence or absence of a biological particle of interest in a given sample (blood, urine, saliva, and the like). Traditional methods for identifying the presence of biological particles of interest in a biological sample have included those in which a particle containing a ligand that binds to the particle of interest (i.e., a binding particle) is incubated with a sample that may or may not include a biological particle of interest. Whether or not the particle of interest is present is traditionally determined by looking for the presence of the conjugate/complex of the binding particle and the particle of interest.

There are limitations associated with looking for the presence of the conjugate/complex. The methods described herein allow one to determine the presence or absence of a biological particle of interest in a given sample (blood, urine, saliva, and the like) by looking for the absence of the binding particle, rather than the presence of the conjugate/complex of the binding particle and the particle of interest. This can be accomplished in at least two different ways.

In one aspect, one can add equal volumes of a colloidal suspension that includes the binding particles to a given volume of a sample which may or may not contain a biological particle of interest and to a control sample (i.e., containing no particles of interest). One can then count the number of binding particles in both colloidal suspensions, and determine the presence of one or more particles of interest by any difference in the number of binding particles.

In another aspect, one can provide a colloidal suspension that includes a known ratio of binding particles and non-binding particles (i.e., particles which do not have the ability to bind to a particle of interest or any other particle in the suspension, and which can be distinguished from the binding particles). After incubating a quantity of the colloidal suspension with a sample which may or may not contain a biological particle of interest, one can count the numbers of binding particles and non-binding particles, and determine whether the ratio of these particles has changed.

The device described herein is particularly applicable to the methods described herein. That is, when the binding and non-binding particles are latex particles, which have a size between about 0.7 to 2 microns and a refractive index of around 1.59, one can determine, based on forward scatter and total extinction, whether a particle passing through the plane of light is a binding particle or a non-binding particle. However, so long as the binding particle and non-binding particle have at least one measurable parameter that is different between the two particles, the absolute numbers of both types of particles can be determined, and the ratio of binding to non-binding particles determined. Examples of measurable parameters include the ratio of forward scatter to total extinction, particle size, refractive index, closeness of fit of a measured pulse to a Gaussian shaped mathematical pulse, and fluorescence (for example, where the two particles are labeled to fluoresce at different wavelengths).

The types of particles that can be directly measured include red blood cells, cancer cells, stem cells, unstable lipid micelles, liposomes, bacteria, yeast, fungi, latex dispersions, human chromosomes and genomic DNA, and extremely large proteins (i.e., those with a size greater than about 0.1 microns). If a binding particle binds to a particle of interest with a significantly small particle size (i.e., less than 10-20% of the size of the binding particle itself), the particle size difference may not be sufficiently large to measure. Accordingly, when seeking to identify the presence or absence of a protein or a virus, it can be advantageous to use two types of binding particles, where each of the binding particles binds to a different site on the protein or virus. In this fashion, the biological particle can act as a linker between two binding particles. The resulting complex (first binding particle—particle of interest—second binding particle) need not be measured, but rather, the absence of the first, second, or both binding particles is measured, relative to the unchanged concentration of non-binding particles in the colloidal suspension.

In one aspect of this embodiment, additional types of binding and/or non-binding particles can be present. When an additional non-binding particle is present, it can function to identify the type of assay being performed. That is, to avoid any confusion as to what test was performed, the second type of non-binding particle can confirm that the positive or negative test result related to a specific test. A plurality of such particles can be used as a "bar code" for the particular assay, where the type and/or relative concentration of particles identifies the assay being performed. When additional binding particles are present, the assay can determine the presence or absence of two or more different types of particles of interest.

In a third embodiment, the present invention is directed to kits useful for conducting the analytical methods described herein. In one aspect of this embodiment, the kits include a colloidal suspension of a binding particle, with instructions for use (i.e., incubating a known volume of the colloidal suspension with the same volume of a sample to be analyzed and a control sample, and counting the number of binding particles in each sample). In another aspect of this embodiment, the kits include a colloidal suspension of a binding particle and a non-binding particle, at known concentrations. The kits can further include instructions for their use (i.e., incubating a volume of the colloidal suspension with a sample to be analyzed, counting the numbers of binding and non-binding particles, and determining the presence or absence of one or more particles of interest by a change in the ratio of binding to non-binding particles. In a third aspect, the kits include additional binding and/or non-binding particles.

BRIEF DESCRIPTION OF THE FIGURES

FIG. 1a is shown with a linear scale, and FIG. 1b is shown with a logarithmic scale. The incident beam from the left is at 660 nm wavelength, the incident intensity is 1 W/m$^2$, and the plane wave is unpolarized. 1a.) Linear Scale: Max=2.10×10$^{-10}$ Watts, Min=0 Watts. 1b.) Log Scale Max=2.10×10$^{-10}$ Watts, Min=2.10×10$^{-18}$ Watts.

In FIG. 5, the axis is drawn in logarithmic space.

FIG. 10 is a schematic illustration showing a pre-cell chamber where hydrodynamic focus can be achieved.

FIG. 11 is a schematic illustration showing one embodiment of the device described herein.

FIG. 12 is a schematic illustration of an electro-optical system, showing the light path and the path of the electrical signal.

DETAILED DESCRIPTION

Figure 1:
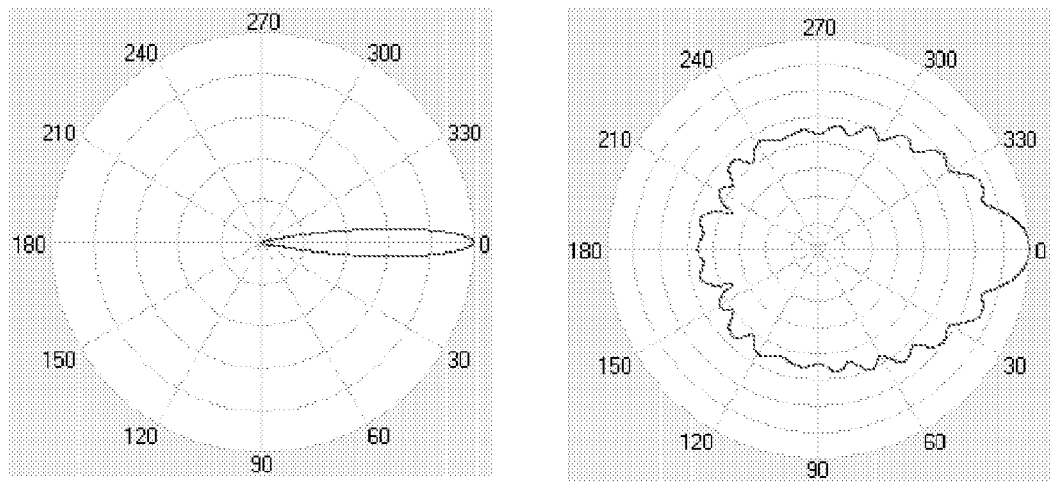
FIGS. 1a and 1b show Mie scattering intensity from a 2 µm Diameter Latex Sphere in 25° C. water.

A device for determining the number of particles in a colloidal suspension is disclosed. Methods for determining the number of particles, including biological particles, in a colloidal suspension are also disclosed, as are methods of determining information on the biological particles. Kits for conducting biological assays are also disclosed. The individual embodiments of the invention are described in more detail below.

The present invention will be better understood with reference to the following definitions.

DEFINITIONS

As used herein, the term "sample" is used to refer to a colloidal suspension (a) that may or may not contain one or more particles of interest (a1), which can be a biological particle of interest. Ideally, a sample includes more than one type of particle, and may include particles of no interest (a2). It is typically important to be able to distinguish the particles of interest from the particles of no interest.

As used herein, the terms "active beads" or "binding particles" are used to define particles that include at least one moiety that enables the bead or particle to bind to a particle of interest. In some calculations used herein, these beads or particles are denoted (b1). In some embodiments, the beads have a single moiety capable of binding a particle of interest, and in other embodiments, the beads have a plurality of moieties capable of binding a particle of interest.

As used herein, the term "active agent" is used to refer to the modification of a bead with a specific molecule that will selectively interact with a specific molecule, receptor and the like on the biological particle of interest.

As used herein, the term "conjugate" is used to refer to the modification of a bead surface by the addition of a ligand to the bead surface. The manner of addition may be through passive binding or through chemical linkage. Passive binding of the ligand to the surface is much less desirable because of the slow loss of the ligand from the bead surface through dissociation of the ligand.

As used herein, the term complex is used to refer to the interaction between a conjugated bead and a biological particle of interest.

As used herein, the terms "marker beads" or non-binding particles" are used to define particles that do not include a moiety that enables the bead or particle to bind to a particle of interest. In some calculations used herein, these beads or particles are denoted (b2).

As will be apparent when considering the analytical methods described herein, when one incubates active beads with a biological particle of interest, and counts the number of marker beads, that number reflects the number of marker beads that have not formed a complex with a biological particle of interest. The complex, or conjugate, of the active beads and the biological particles of interest is sometimes referred to herein as a complex or conjugate.

As used herein, the terms "colloidal suspension of active and marker beads" and "colloidal suspension of binding and non-binding particles" refer to colloidal suspensions that contains at least two populations of beads/particles. In some calculations used herein, these colloidal suspensions are denoted (b). One population (b1) is composed of spheres whose diameters are known in advance, and whose size distribution has a very small standard deviation in diameter space (i.e., the particles can be considered to be "mono-sized"). A second population (b2) in the colloidal suspension (b) is another mono-sized population of a different mean diameter than the first population. The particles/beads (b2) can be of the same diameter as the first population (b1) provided that they have a different index of refraction, or can be distinguished based on some other criteria.

It is important that the two bead populations (b1 & b2) be of substantially the same density. It is advantageous to have the two populations (b1 & b2) be as close as possible in size, but still be able to be discerned as belonging to different groups by the measuring instrument. For example, it is preferred that the particles b1 and b2 have a mean diameter that does not differ by more than 0.5 microns or less than 0.2 microns, and, ideally, differs by between about 0.2 and 0.3 microns, with both diameters falling within the range of between about 0.7 and 2 microns.

As used herein, the term "a particle of interest" is intended to mean one or more particles of interest. That is, if a particular sample contains a particle of interest, it is likely that the sample will also contain more than one biological particle of interest. In theory, the presence of a single particle of interest bound to a single active bead can be identified by looking at the absence of the single active bead, but in practice, it will likely be the case that a plurality of particles of interest bound to a plurality of active beads.

As used herein, the term "library" refers to the collection of different particle attributes that may be used to distinguish, differentiate and identify biological particles. A library is also defined by more than 3 parameters and more than three different particles, preferably more than ten different particles, and, most preferably, more than one hundred different particles.

As used herein, the term "epitope" refers to the presence of a specific molecule or group of molecules present on a particle surface that may from an identifiable biomarker such as a receptor, binding site, and the like.

As used herein, the term "genetic probe" refers to a sequence of DNA bases complimentary to a specific sequence within DNA. This probe may be chemically linked to a bead to from an active bead as describe previously.

As used herein, the term "measuring instrument" refers to any instrument that can distinguish between particles in the two bead populations, regardless of how the beads are distinguished, and which can count the particles in the two bead populations. The measuring instrument can be, but need not be, a single particle optical sensor. Representative measuring instruments include the device described herein, a coulter counter, a flow cytometer, a hematology analyzer, a dynamic light scattering analyzer, a centrifuge analyzer, and any other device capable of measuring one or more properties of colloidally-suspended particles.

As used herein, "transit time" can be measured from the time of the data sample, whose representation of voltage is greater than some arbitrary threshold, to the time when that voltage dropped below the same threshold.

I. Device for Measuring Light Extinction and Forward Scatter

In one embodiment, the present invention is directed to a new device capable of measuring light extinction and forward scatter of particles present in a colloidal suspension as they pass through a sensing zone.

The device can measure particles over a wide range of particle sizes, from 0.5 to 100 microns, but is particularly useful for measuring particles in the size range of between about 0.7 to 2 microns. In this particular size range, particles with different refractive indices (such as biological cells, with a refractive index of around 1.39 and latex particles, with a refractive index of around 1.59) are easily distinguished. The device offers various advantages over a conventional flow cytometer.

The device includes a flow cell, a forward scattering detector, an extinction detector, a light-generating element capable of generating a plane of light, such as a laser light passing through a cylindrical lens, collection optics for the scatter detector which allow the user to collect information on a predefined set of forward angles, and a fluid transporting element for transporting fluid through the flow cell. The predefined set of forward angles are approximately 15 to 30 degrees as measured from the axis formed by the direction of travel of the beam of light and the particle in the sensing zone.

The device can also include an element for producing hydrodynamic focus of a sample fluid flow, wherein the element for producing hydrodynamic focus is disposed between the fluid transporting element and the flow cell. The element for producing hydrodynamic focus can include, for example, a sample feed tube and a sheath feed tube. The sheath feed tube typically encloses the sample feed tube, and fluid eluting from it guides the sample eluting from the sample feed tube. This also allows one to rapidly clean the equipment between runs, by flushing the system with a clean fluid that does not include particles.

In some embodiments, the sample can be passed through the device undiluted. In other embodiments, it may be advantageous to dilute the sample, for example, by introducing hydrodynamic flow. It may be easier to ensure that all particles are passed through the instrument when the colloidal suspension is diluted in this fashion, although it is not necessary for the correct functioning of the instrument, and an instrument can be designed without a hydrodynamic flow element.

The device can also include an element for storing the sample internally in the form of a storage loop or coil made of tubing material, or other storage chamber.

The device can also include fluid input ports to allow the introduction of a transport fluid, a cleaning fluid, a sterilizing and other agents into the device.

The device can also include an element for calculating one or more values selected from the group consisting of particle size, particle transit time, and pulse fit parameter. These values are calculated based on information related to forward scatter and extinction of light interacting with particles flowing through the device, based on a series of calculations described in detail herein.

In one aspect of this embodiment, the light-generating element includes a laser and a lens, wherein the lens provides a planar light output. For example, the lens can be a cylindrical lens.

The fluid transport element can be a pump, for example, a syringe pump. The device can also include a second fluid transport pump for transporting sheath fluid to the sheath feed tube. This second fluid transport pump can be any type of pump, but is preferably a metered dispense pump.

The device can also include a library of information related to one or more values selected from the group consisting of forward scatter intensity, extinction intensity, particle transit time, and pulse fit parameter. This library can be in the form of an in-silico "look-up table." This type of table can take information on forward scatter intensity and extinction intensity for each particle and produce information on both index of refraction and particle size. Accordingly, in addition to counting the number of particles, the device can calculate the particle size of the particles, as well as their index of refraction. This information can be used as described herein in a number of biological applications.

Ideally, one or more of the forward scattering detector and the extinction detector is a silicon photodiode detector and/or neither the forward scattering detector nor the extinction or total scatter detector is a PMT (photomultiplier tube) or APD (avalanche photodiode) detector.

Silicon detectors can be preferred, because they can handle the relatively large amount of light resulting from the laser light, particularly in the extinction signal path. Briefly, silicon photodiode detectors are semiconductor light sensors that when light hits them they generate a current in the P-N junction in the semiconductor. A P-N junction is a junction of P-type and N-type semiconductor. Silicon detectors provide a means of transforming light energy to an electrical current, using the small energy gap between the valence and conduction bands of the detector. When light with enough energy to excite an electron from the valence to the conduction band is incident upon the detector, the resulting accumulation of charge leads to a flow of current in an external circuit.

When using both a scattering and extinction detector to measure particle attributes, it is important, when seeking to determine derivative information (such as particle size and index of refraction) to have a distribution of intensities that is acquired using both detectors. The typical size range measured using scattering is between about 0.5 and about 2 microns for refractive index 1.59 latex beads. The typical size range measured by an extinction detector is about 0.7 to about 200 microns for refractive index 1.59 latex beads. The overlap region is typically between about 0.7 to about 2 microns. Therefore, the ideal particle size measured using the device described herein is in this size range (i.e., between about 0.7 to about 2 microns) for refractive index 1.59 latex beads.

Having a priori calculated table of scattering and extinction intensities for all of the index of refractions for particles one is likely to encounter in the current instrument geometry, then if one plots forward scatter and total scatter on an x-y axis, the intersection provides the index of refraction and the diameter of the measured particle. This works if one restricts themselves to a known and fixed geometry of light collection, as is described herein, and to particles whose index of refraction is known (i.e. latex beads), or can be bound within a range of index of refractions (i.e. biological particles). Otherwise given the nature of light and scattering and extinction intensities at these energies, there can be ambiguity as to size and index of refraction. Thus, one can measure the index of refraction of a particle by the ratio of energy in the forward direction versus total scatter (f/t) within the overlapping region of the detectors. One can measure particle size in the same way. This is considered derivative information, as it is not directly measured by the instrument. It is possible to calculate this derivative information contemporaneously with use, but it is not practical as light scattering calculations are time consuming, given current state of the art hardware and software. A look-up table is the preferred method of assigning an index of refraction and a size to a particle. In one embodiment, this "lookup table" is an in-silico "look-up table" that takes information on forward scatter and total scatter for each particle and produce information on both index of refraction and particle size.

These and other aspects of the device are described in more detail below. The device can be used to evaluate colloidal suspensions of particles, for example, to identify the presence or absence of particles of interest.

II. Biological Particles of Interest

Cells are one type of biological particle that can be detected. The method can be used to determine the presence or absence of a specific type of cell in a given sample. For example, a sample of blood, urine, pleural fluid, spinal fluid, and the like can be evaluated for the presence or absence of bacteria, fungi, and the like. The particle size, and, optionally, particle shape, can also provide information about the specific type of bacteria, fungi or virus.

In one embodiment, suitable information on the particles can be obtained simply by obtaining information on particle size and distribution. That is, one can frequently determine the presence or absence of certain biological particles present in the sample medium with this information. For example, specific bacteria, fungi, or viruses can be identified solely on the basis of their size, and liposomal suspensions can be evaluated for agglomeration solely on the basis of the size of the agglomerated particles.

In other embodiments, where there is an interest in determining whether a particular agent forms a complex with a particular type of biological particle, additional information may be required. That is, one can determine the presence or absence of a particular cell type, or an ejected particle from a type of cell, by forming a complex between a) the cell or ejected particle and b) an active agent conjugated to a microparticle or nanoparticle ("conjugate"). The complex has a larger particle size than the cell, the ejected particle, or the conjugate, so the use of a suitable optical sizing technique can determine whether a complex was formed.

In some aspects of this embodiment, the biological particle is a cell that expresses a specific receptor, and the techniques permit high throughput screening of putative therapeutic agents that bind to the receptor.

In other aspects of this embodiment, the biological particle comprises cells from a patient, for example, blood cells, endothelial cells, stem cells, other cells shed from specific organs into the blood, spinal fluid and the like, or cancer cells, and these cells are incubated with putative therapeutic agents. Agents that bind to the cells can potentially be useful as therapeutic agents for the patient. Accordingly, this embodiment provides personalized medicine approaches.

In some of these embodiments, two spectra are taken. The first is taken on the sample media before complex formation, and the second is taken after complex formation, so one can look for the difference in particle size and distribution. However, in other embodiments, where the complex has a known particle size, and all that is required is to show that the complex formed, one can simply incubate the biological particle and the substance which may or may not form a complex with the biological particle, and use the techniques described herein to determine whether the complex was formed.

III. Active and Marker Beads

The active and marker beads can be formed of any suitable material that has a significantly different refractive index than the biological particles of interest. Since most biological particles of interest have a refractive index of around 1.39, any material can be used to prepare the active and marker beads that has a refractive index of at least 1.50 or higher, and ini one embodiment, is in the range of about 1.2 to about 1.8.

In one embodiment, the particles are metallic particles, although metallic particles, such as gold and silver particles, tend to fall between latex and biological particles when placed on a graph of total vs. forward scatter energies.

Representative particles include latex particles, glass, and those made of metals such as gold, silver and the like. The particles can be latex particles with a gold or other metallic coating. The particles can be formed from any other non-reactive compound or mixture.

In this context, "non-reactive" means particles having no active chemical binding sites on their exposed surfaces that can bind with each other or to other members of the colloidal suspension while in use in the analytical methods described herein. The formation of active beads using these non-reactive particles, which includes one or more moieties, would require further modification of their surface chemistry.

In one embodiment, where there would otherwise be non-specific binding to the particles (i.e, binding other than through the reaction of a receptor on a particle of interest with a ligand on an active bead), such non-specific binding to both the active and marker beads, typically by unwanted proteins, is inhibited by adding bovine albumin to the suspension of the particles. The active bead should specifically interact with an agent on the targeted particle. That interaction constitutes the "reaction". The non-active beads (i.e. inert beads or marker beads) do not "react" with anything.

The active beads include one or more moeities capable of forming a complex with a biological particle of interest. The nature of these moieties depends on the nature of the biological particle of interest. Where the particle of interest includes a receptor, then the active bead includes one or more ligands known to bind to the receptor.

Where the particle of interest is genomic DNA, the active bead includes one or more primers capable of forming a complex with a site on the genomic DNA that includes a mutation of interest, if such mutation is present.

Where the particle of interest is a protein, and the protein has a particle size greater than about 0.5 microns, the moiety is capable of binding to/complexing with the protein. If the particle of interest is a protein with a relatively smaller particle size, then there are preferably two types of active beads, each of which is capable of binding to a different site on the protein, such that the resulting complex includes the protein and two or more active beads. The resulting complex has a particle size at least equal to the particle size of the two active beads, plus the size of the protein of interest, and can thus be measured even if the protein itself is not large enough to significantly alter any of the detectable parameters of a single bead following complex formation with that bead.

IV. Kits

In one embodiment, the kits include a single type of active bead, linked to a single copy of a single moiety capable of binding to a single biological particle of interest. In one aspect of this embodiment, the kits further include marker beads, where the ratio of active to marker beads is known. Ideally, the ratio of active to marker beads is in the range of 0.5:1 to 1:0.5. In another aspect of this embodiment, the kits further include one or more particles that function as a "key," to identify the type of assay being performed. Such "key" particles have a measurable property different from the active and marker beads, for example, a different density, refractive index, particle size, fluorescence, and the like.

In a second embodiment, the kits include two types of active beads, each of which is linked to a single moiety capable of binding to a single biological particle of interest. In one aspect of this embodiment, the two types of active beads have a different particle size. In this aspect, the active beads can be used to complex with different types of biological particles, or, particularly in the case of relatively small biological particles, can both form a complex with a biological particle, through a different binding site, and allow one to measure relatively small biological particles, for example, proteins with a particle size less than about 0.5 micron.

In one aspect of this embodiment, the kits further include marker beads, where the ratio of active to marker beads is known. Ideally, the ratio of active to marker beads is in the range of 0.5:1 to 1:0.5. In another aspect of this embodiment, the kits further include one or more particles that function as a "key," to identify the type of assay being performed. Such "key" particles have a measurable property different from the active and marker beads, for example, a different density, refractive index, particle size, fluorescence, and the like.

In a third embodiment, the kits include a single type of active bead, linked to more than one copy of a single moiety capable of binding to a single biological particle of interest. In one aspect of this embodiment, the kits further include marker beads, where the ratio of active to marker beads is known. Ideally, the ratio of active to marker beads is in the range of 0.5:1 to 1:0.5. In another aspect of this embodiment, the kits further include one or more particles that function as a "key," to identify the type of assay being performed. Such "key" particles have a measurable property different from the active and marker beads, for example, a different density, refractive index, particle size, fluorescence, and the like.

V. Methods of Identifying the Presence or Absence of Particles of Interest in a Given Sample A colloidal suspension (a), which may or may not contain biological particles of interest (a1) and may also contain particles of no interest (a2), is mixed with a second colloidal suspension (b) containing a combination of active and marker beads (b1 and b2).

Mechanical agitation is applied to mix the two aliquots into a homogeneous suspension (c). The suspending or transport fluids are chosen so as to be miscible, and a sufficient time is allowed to pass, at a sufficient temperature, and under sufficient conditions, for biological particles of interest to bind to active beads (i.e., a1+b1 form a complex). The resulting sample is introduced to an instrument in order to count the number of un-bound active beads. A precise volume taken from suspension (c) is processed through the instrument.

The number of beads in the given volume will be expected to vary, depending on the concentration of the particle of interest. With tumor cells, the number of beads would likely be relatively low, whereas with platelets, the number would be relatively higher. The get the correct # of beads, the volume of sample and the volume of beads may vary.

The colloidal suspension (b) contains at least two populations. One population (b1) is composed of spheres whose diameters are well known in advance and their size distribution has a very small standard deviation in diameter space. They are essentially considered to be mono-sized.

A second population (b2) in the colloidal suspension (b) is another mono-sized population of a different mean diameter than the first population. The beads can be of the same diameter as the first population (b1), provided that they have a different index of refraction, or some other measurable property that distinguishes b1 from b2.

It is important that the two bead populations (b1 & b2) be of substantially the same density. It is advantageous to have the two populations (b1 & b2) as close as possible in size, but still be able to be discerned as belonging to different groups by the measuring instrument.

The active and marker beads can be formed of any suitable material that has a significantly different refractive index than the biological particles of interest. Since most biological particles of interest have a refractive index of around 1.39, any material can be used to prepare the active and marker beads that has a refractive index of at least 1.50 or higher. Representative particles include latex particles, and those made of metals such as gold, silver and the like. The particles can be latex particles with a gold or other metallic coating. The particles can be formed from any other non-reactive compound or mixture.

In this context, "non-reactive" means particles having no active chemical binding sites on their exposed surfaces that can bind with each other or to other members of the colloidal suspension while in use in this instrument. The formation of active beads using these non-reactive particles, which includes one or more moieties, would require further modification of their surface chemistry.

Concentration Ratio.

The concentration ratio of the two populations (b1 & b2) is ideal when it is equal in concentration, so that the same number of mono-sized beads (b1) is present in the colloidal suspension as beads of type (b2). However other ratios can also perform the function with diminished accuracy. A suitable range of concentration ratios is 1:0.5 to 0.5:1, with 1:1 being ideal.

Function (b1)

The bead population (b1) in colloidal suspension (b) has been chemically altered prior to inclusion in this suspension to contain active binding sites (ligands) on their surface. Ideally one bead per biological particle is desired. However, it typically requires multiple ligands per bead-particle interaction to provide enough binding energy to stabilize the complex formation. The number of ligands required depends on the size of the bead and the strength of the ligand-receptor interaction. In some situations, for example, when identifying molecules like DNA or von Willebrand factor, it may be advantageous to have multiple beads bound to the biological particle. The extent of binding of beads to the particle will be basically governed by the relative concentrations of the beads to the particles and by the coordination number of the binding [i.e., how many beads can be coordinated to a given particle. This may, in turn, be governed by the size of the bead to particle (steric hindrance) and by the number of ligand-receptor interactions].

The binding sites on the active beads are specifically designed so as to bind with specific receptors on the biological particles of interest. The binding sites on the active beads (b1), after some chemical equilibration time, mate with receptor sites on the surface of the sample suspension (a1), and form a paired set linking the two particles together (a1+b1).

Function (b2)

The function of the second group (b2) in the marker bead population is to provide a measure of quality of the packaging, transport, storage and use of the colloidal suspension (b). Any forces that would deplete the population of beads in suspension (b) would be identified by their effect on the population of marker beads (b2). If beads are removed (lost) due to a leak, or trapped in a fluid fitting during transport, or stuck to the edge of the bottle due to improper handling, then the same quantity (or quantity ratio) is expected to be lost from population (b1) as are lost from population (b2). Since population (b2) has no active means of binding to anything, then they become the measure of successful colloidal transport of fluid (b) from manufacturer to the point of use.

Other Beads

It is possible, and even desirable, to add one or more particles, with the same or varying populations in terms of number and particle diameter, to the colloidal suspension (b). In one embodiment, such particles are added for the purpose of identifying the suspension to the measuring instrument. In one aspect of this embodiment, the presence of such particles provides a "key" that activates specific software that recognizes the specific assay to be performed, and, optionally, activates an appropriate robotic program to run the assay). Provided that the beads added are far apart in measurable parameters that they do not interfere with the function of bead groups (b1) and (b2). For this group of additional beads (b3, b4, b5 . . . ), it is not necessary that they be of the same density or makeup as bead groups (b1 & b2).

Shape

For the purpose of this instrument, spherical particles (populations b1, b2, b3, b4 . . . ) work best since their orientation does not matter as they pass through the sensing zone of the measuring instrument. Spheres are also easier to manufacture and a highly accurate supply is commercially available. However other shapes are possible provided that there is enough separation of the components in data space once they are detected by the instrument.

Sensing Zone

The mixed suspension (c) is transported through the instrument tubing, via pumping action, into a sensing zone. This sensing zone is composed of a quartz glass cell where the particles in the suspension travel inside a flow channel at the center of the glass cell, perpendicular to a beam of light. The light source generating the beam of light is typically a monochromatic laser in order to minimize chromatic aberrations in the collecting instrument optics, with an Intensity profile that is Gaussian. The light beam can be focused in one dimension to form a line of illumination via the use of a cylindrical lens placed between the quartz glass flow cell and the laser light source. Said lens is placed at a precise distance away from the flow cell, so that the focal point of the light occurs inside the flow cell, and in the center of the flow channel.

In one embodiment, just before the particles travel into the quartz glass cell, the flow of the mixed suspension (c) is surrounded by a particle-free fluid (typically water) for the purpose of protecting the walls of the cell from getting dirty (over time) and for the purpose of lining up all the suspended particles so that they may be sensed one at a time in the sensing zone. The sensing zone is the volume of intersection between the beam of light coming from the laser and the particle stream formed in the center of the fluid flow. This concentric flow (transport fluid on the outside, and colloidal suspension (c) on the inside), if forced through a tube of diminishing diameter, accelerates in velocity, and the colloidal suspension is reduced in diameter. This process is called hydrodynamic focusing, and it ensures that the particles to be measured travel through the center of the cell, and, hence, through the optimal sensing volume. Hydrodynamic focusing is well known in the field of flow cytometry.

Detection

As a particle finds itself alone in the view volume, illuminated by the laser light, it mostly scatters light in all directions (FIG. 1), and also absorbs some of the energy. The instrument uses two detectors to measure this event. One capturing scattered light in the forward direction (SD—Scatter Detector) (comprising any light exiting in the cone of 15° to 30° as measured from the central axis formed by the direction of travel of the beam, and the center of the particle), and a second detector measuring the totality of light scattered and absorbed away from the beam of laser light (ED—Extinction Detector).

In one embodiment, some particles will be detected by only one of the detectors, and not the other. If the particle is small, beyond the lower detection limits of the extinction detector, but large enough to be within the detection limits of the scatter detector, only scattering intensity information about the particle will be obtained, and no extinction intensity information will be obtained. If the particle is large, and therefore scatters too much light, it will saturate the scatter detector, and only extinction information will be available. In cases where there is information from only one detector, we know that the particle is not one of the active (b1) or marker (b2) particles, and can be excluded. The instrument can report to the user that it tabulated such a particle, and may include it in a graphical representation.

It is also possible that there will be particles of such small size that neither detector will detect them as they pass through the sensing zone. Since they can not be detected, they do not contribute to the data gathered by the instrument.

Collection Optics

Figure 2:
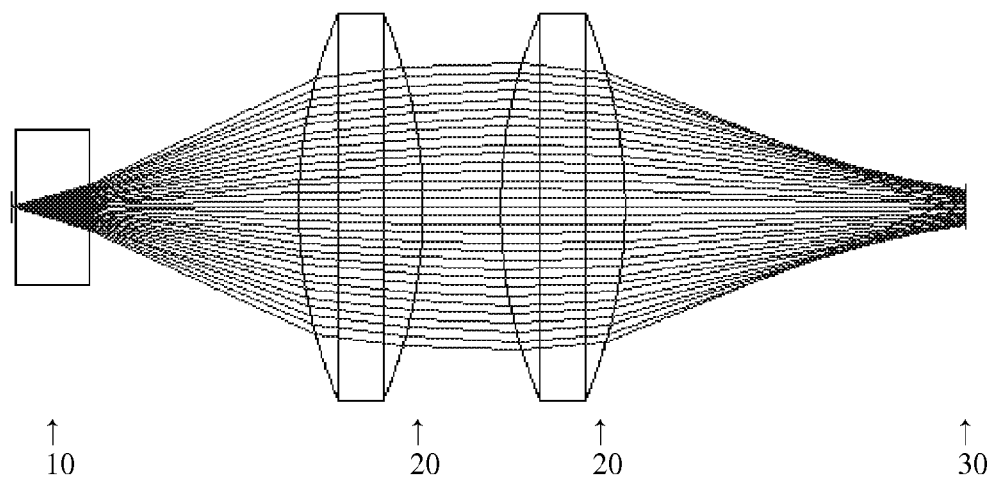
FIG. 2 is a diagram showing forward scatter light and collection optics. Light scattering from a particle inside the flow cell (10) is steered to the scattering detector (30), by means of double convex lenses (20) that serve to capture and redirect the forward scattered light into the detector (30). A minor deflects the light beam as it exits the cell toward the extinction detector (not shown).

Light is steered to the scattering detector from the sensing volume in the cell, by means of double convex lenses (FIG. 2.) that serve to capture and re-direct the forward scattered light into the detector (SD). There is a mirror deflecting the light beam as it exits the cell toward the extinction detector (ED). This detector measures how much the light beam dimmed when a particle transversed it in the flow cell and subsequently absorbed some of the energy and scattered some light away in all directions.

Analog/Digital Conversion (A/D Conversion).

The two detectors (SD & ED) create a current proportional to the amount of light that falls on their active sensing area. (Typical of Silicone Pin Diode Detectors). This current by means of a trans-impedance amplifier (one for each channel) is converted to a voltage and that voltage is digitized by an A/D for further processing by a computer. This is a practice well known to those skilled in the art.

Data Gathered

Figure 3:
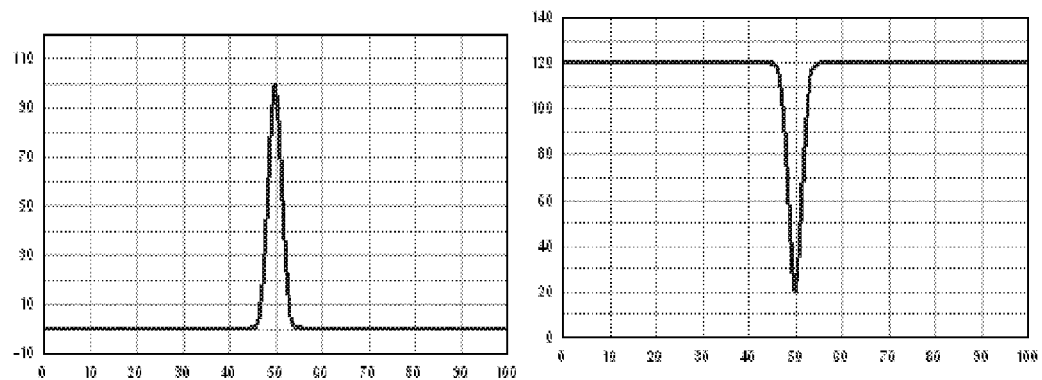
FIGS. 3a and 3b are charts showing the signal generated from a scattering detector (FIG. 3a) and an extinction detector (FIG. 3b), in terms of voltage (mV) vs. time (µsec).

There are two data streams gathered by a computer controlling the instrument. One from the Scatter Detector and one from the Extinction Detector is shown in (FIGS. 3a and 3b). The A/D converters sample frequently enough for there to be a sufficient quantity of samples to describes the pulses generated by the moving particle in front of the light beam. From this raw data several derivative pieces of information can be obtained.

One type of information that can be measured from a particle scattering light in the sensing zone, is the Forward Scattering Intensity and its Extinction Intensity. This is the Amplitude of each of the pulses generated at the detectors by the particle passing through the sensing zone. Each generated pulse is expressed as a number representing a voltage. This amplitude is a measure of the amount of light that made it to the detector (or in the case of the Extinction Detector (ED) the amount of light removed—as extinction signal pulses grow negative).

Amplitude can simply be the largest value within the boundary of the data that describes this pulse, or it can be extracted from a function being fitted to the data set that comprises the pulse. One value of intensity is gathered from each channel for any given particle passing through the sensing zone, such that each particle has a Value for Scattering Intensity and one for Extinction Intensity.

Another derivative type of information that can be extracted from the stream of numbers produced by the A/D converter, is the amount of time a particle took to pass through the light beam (i.e., transit time). The time of transit for a particle can be obtained from the precise interval that the A/D takes to make a measurement (for example, one reading every 500 ns). Transit time can be measured from the time of the data sample, whose representation of voltage, is greater than some arbitrary threshold, to the time when that voltage dropped below the same threshold.

A third piece of information that is related, but not the same as the second, is the width of the pulse at half the pulse height. If all particles passing in front of the detector were spheres, then the value of the width at half height of the pulse would be directly proportional to the transit time measured at the base of each pulse. Particles that are not spheres have a different pulse profile than the typical Gaussian profile of a sphere. It is relevant to note that the expected pulse shape from a spherical particle is Gaussian in nature, because the sensing volume is illuminated with a light beam whose intensity profile is Gaussian.

A fourth piece of information that can be derived is the measure of fitness of a measured pulse to a Gaussian-shaped mathematical pulse having the same magnitude and same base width ($\Delta T$) as the measured pulse. This number is computed and can be expressed as an absolute error (least squares residual), or as a fraction of fit, 1 being a perfect Gaussian pulse.

$$R^2 := \Sigma(y_i - f(x_i))^2$$

Equation. 1. Measure of Error of fit $R^2$ of a function $f(x_i)$ to data set $(y_i)$.

Nature

This invention takes advantage of the way particles suspended in a fluid scatter light at the dimensions of interest and takes advantage of the particles having the refractive indices that they do. Using Polystyrene spheres for the active surface (b1) and marker (b2) beads (RI of 1.59), and selecting the detection geometry specified above (15° to 30° degrees forward scatter collection angles), we are guaranteeing that when the marker and active beads go through the instrument, they will be detected at their expected location, and that biological particles will be detected at regions far enough from the polystyrene beads in data space to be clearly separable by the instrument.

Other diameter spheres and other material compositions for the marker and active beads are possible, and will work in this instrument design. Latex (RI 1.59) beads of diameter 1 μm and 1.3 μm are chosen as examples for the purposes of illustration.

Figure 4:
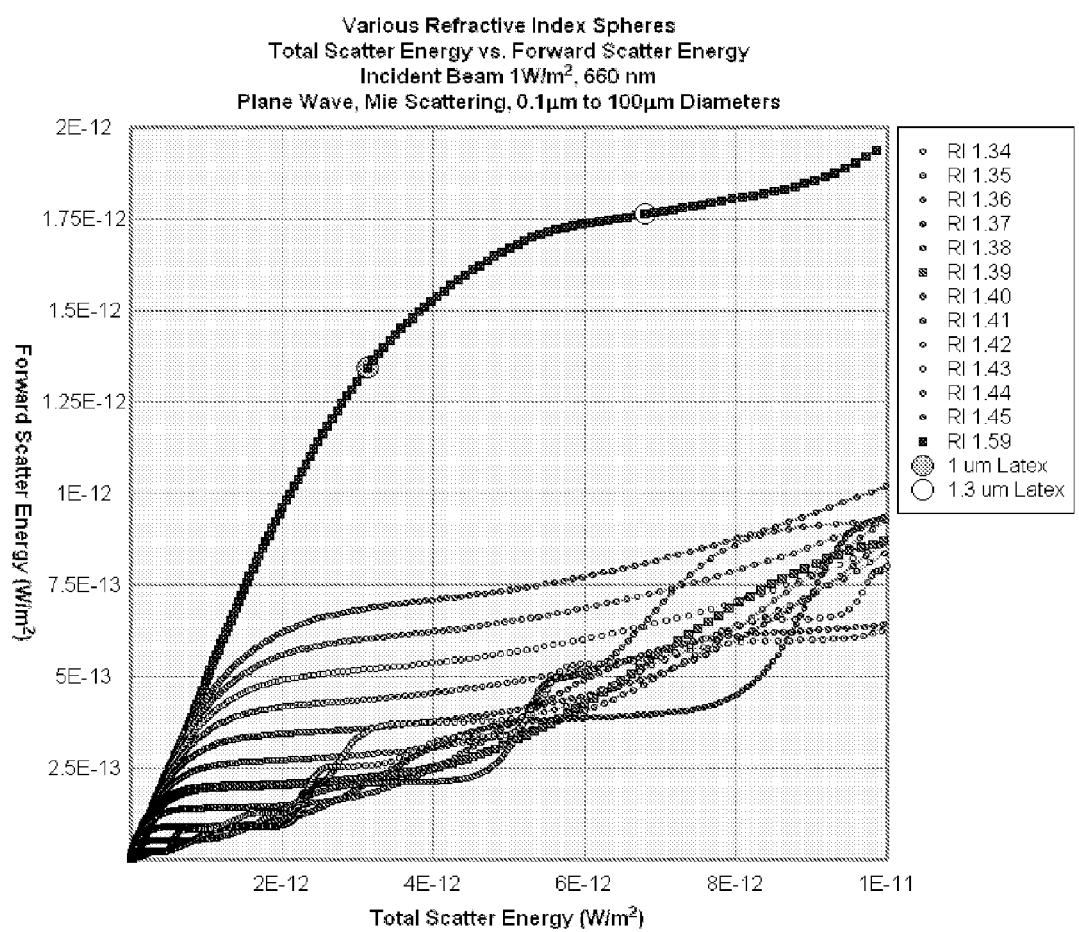
FIG. 4 is a chart illustrating the ISO Refractive Index (RI) curve of RI 1.59 (latex) material (blue in the drawing), and the locations of the two specific sizes, namely 1 µm and 1.3 µm. It also shows the location in the forward vs. total scatter data space of other index material with an RI of from 1.34 to 1.45. The computation is done for particles from 0.1 µm to 100 µm, and shows no overlap in this size range. This is the size range of particles an instrument examining biological particles is likely to encounter. The axis is drawn in linear space.

FIG. 4 illustrates the ISO Refractive Index curve of RI 1.59 (latex) material (blue in the drawing), and the locations of the two specific sizes, namely 1 μm and 1.3 μm. It also shows the location in the forward vs. total scatter data space of other index material. From Refractive index 1.34 to 1.45. The computation is done for particles from 0.1 μm to 100 μm and shows there is no overlap in this size range. This is the size range of particles an instrument examining biological particles is likely to encounter. Axis is drawn in Linear space.

Figure 5:
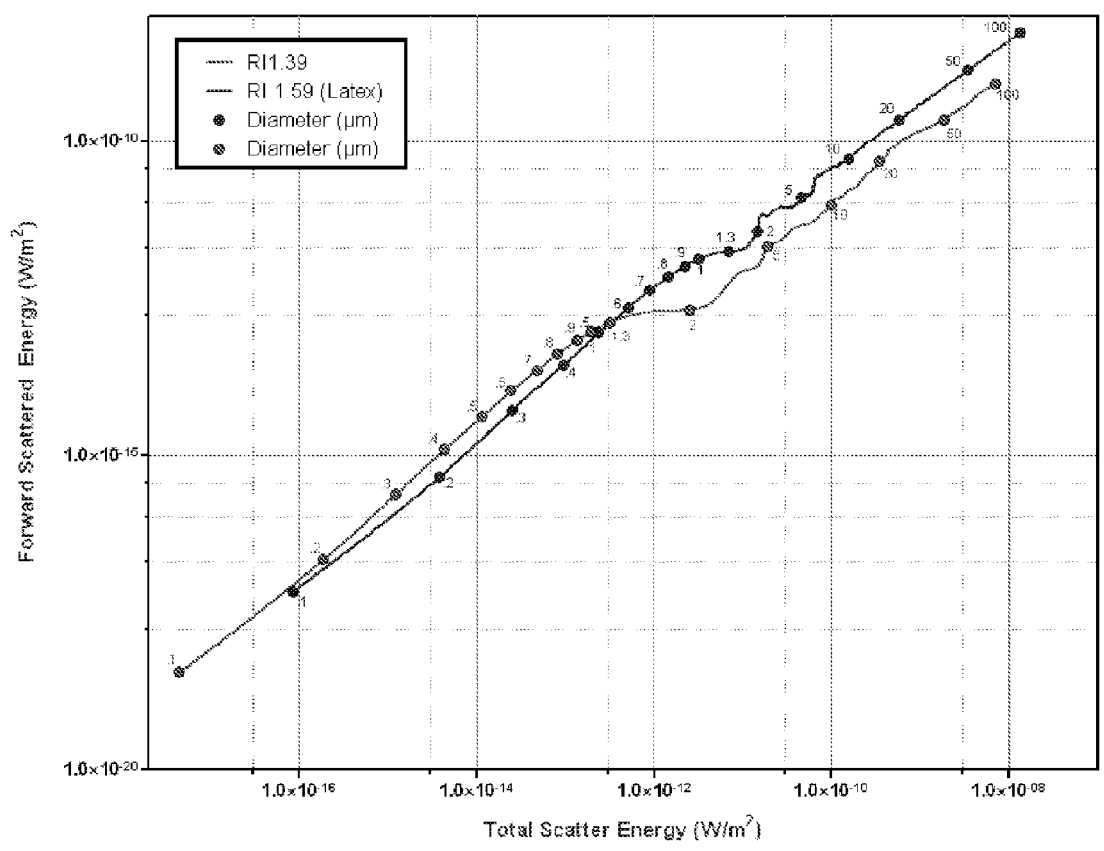
FIG. 5 is a drawing of the same type as FIG. 4 (i.e., total vs. forward scatter intensity), but shows two Index of Refraction curves and the particle size associated with a particular energy. Slight differences in appearance with FIG. 4 are due to the axis scaling chosen.

FIG. 5 is a drawing of the same type (total vs. forward scatter intensity), but shows two Index of Refraction curves and the particle size associated with a particular energy. Slight differences in appearance with FIG. 4, are due to the axis scaling chosen. Axis is drawn in log space.

Figure 6:
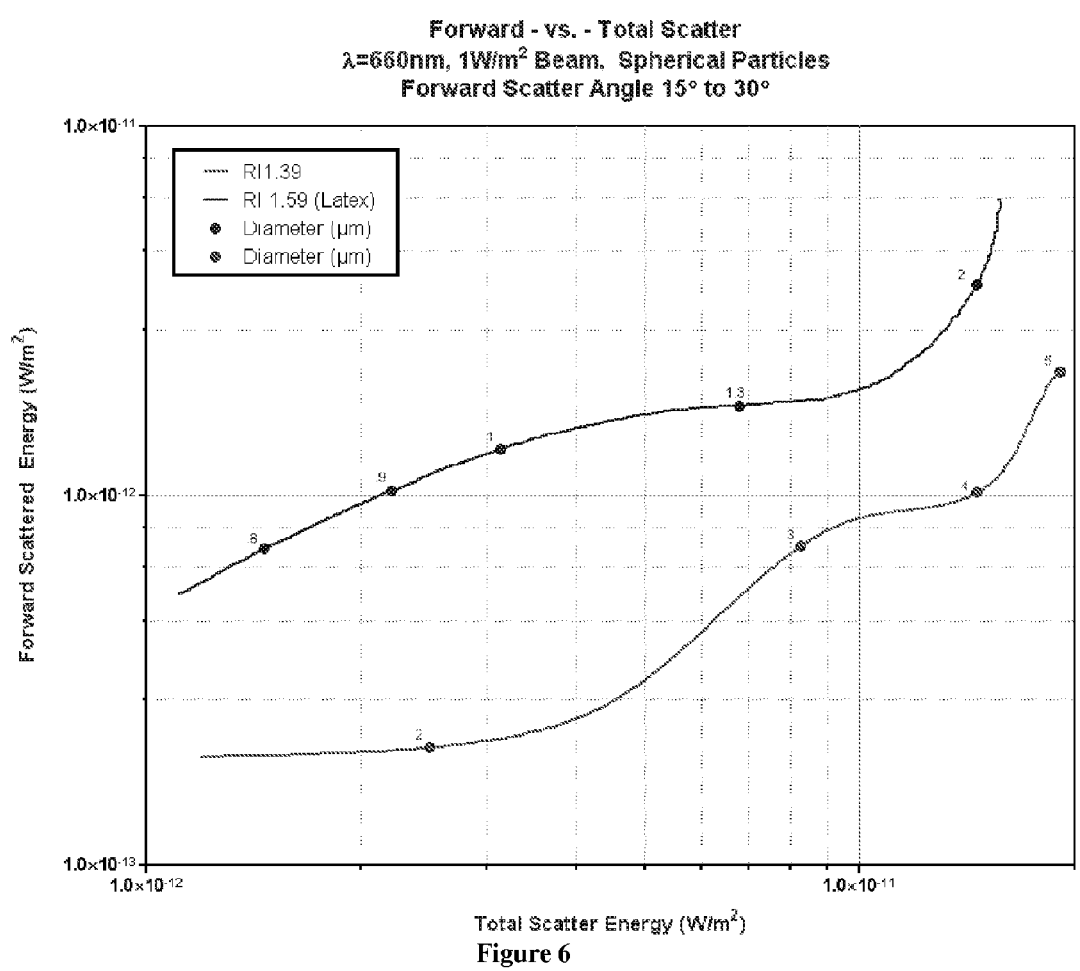
FIG. 6 is a close up FIG. 5, showing in more detail the area of energy surrounding the 1 µm and 1.3 µm particles.

FIG. 6 is a close up FIG. 5, showing in more detail the area of energy surrounding the 1 μm and 1.3 μm particles.

Figure 7:
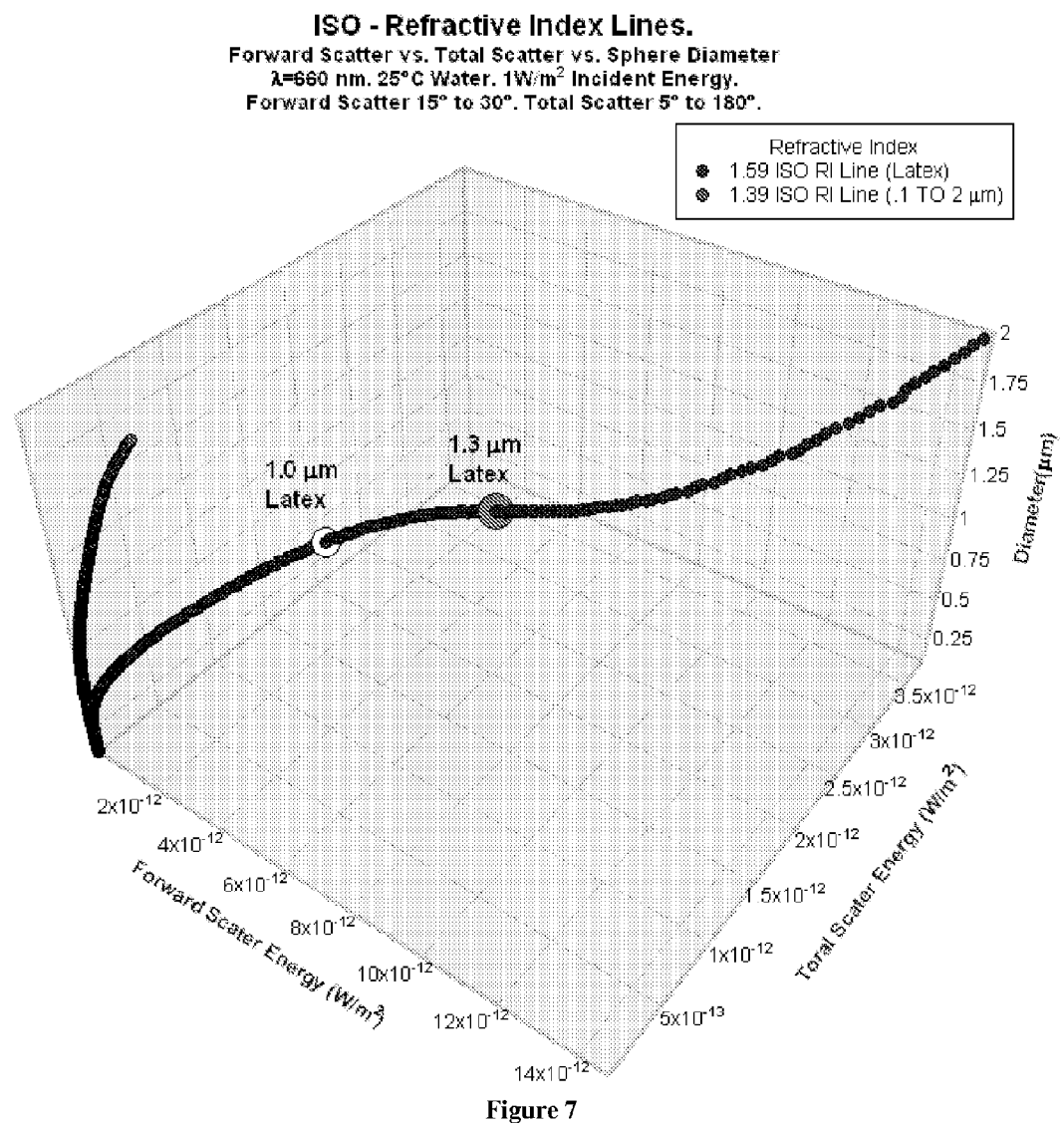
FIG. 7 is a graph of latex (RI 1.59) and RI 1.39 shown in three dimensional (3D) space, using the linear scale. Forward versus total scatter is shown for particles with an RI of 1.39 (biological particles) and 1.59 (latex particles) in 3D space. The two large beads in the graph are of a 1 µm and of a 1.3 µm Latex Particle located in their proper position in this data space. The red line represents particles of 1.39 Refractive Index.

FIG. 7 is a graph of latex (RI 1.59) and RI 1.39 shown in 3D space.

For the purpose of these computations the light used was an unpolarized plane wave, 660 nm in wavelength, and having a power density of 1 W per square meter. Under these conditions, the refractive index of water is 1.33. Most biological particles have a refractive index around 1.39, whereas latex particles have a refractive index of around 1.59.

As can be seen in FIG. 5, for particle sizes in the range of between about 0.7 and about 2 microns, as measured using the parameters described above, there is a significant measurable difference between the ratio of forward scatter and total scatter for particles with different refractive indices. Since there are a number of biological particles in this size range, and it is relatively easy to produce latex and other non-biological particles in this size range, the technique allows one to measure the number of latex or other non-biological particles, and the number of biological particles, and easily differentiate the two populations of particles. Thus, by using active and marker particles within this size range, one can count the number of such particles before and after incubation with biological particles of interest, even in the presence of biological particles with the same particle size.

While the biological particles and the active and marker beads will fall within the particle size range, and the active and marker beads have a different refractive index than the biological particles, one can but need not measure the refractive index or particle size. Rather, one can simply count particles with a measurable parameter, such as the ratio of forward scatter to total scatter (or total scatter to forward scatter), and identify into which "box" the particles belong. That is, one can determine whether a particle is a biological particle, an active bead, or a marker bead.

Plotting the Data

If desired, one can determine the particle size and/or refractive index from this information, and can provide a plot of particle size and refractive index. This plot will show the relative numbers of non-complexed biological particles, active beads and marker beads. Representative plots are shown in FIGS. 5 and 6. One can also plot the information in three dimensions, for example, using forward scatter, total scatter, and particle diameter, if desired. A representative plot is shown in FIG. 7.

However, the absolute answer of whether or not a sample included a biological particle of interest depends solely on the number of such active and marker beads before and after the active beads are incubated with a sample that may or may not contain a particle of interest.

Data Space

Once a particle has traversed the sensing zone, primary information can be obtained on each particle, such as its Scatter Intensity, Extinction Intensity, Transit Time, Gaussian Fit parameter, and the like. This information the computer can proceed to evaluate and categorize the particle.

A detected particle will typically fall into one of several categories (types).

i) It will be an active particle (b1) unattached to anything. It will have the forward scatter intensity, extinction intensity, transit time, and Gaussian fit parameter typical of unattached active particles.

ii) It will be a marker particle (b2). It will have the forward scatter intensity, extinction intensity, transit time, and Gaussian fit parameter typical of marker particles.

iii) It will be a biological particle of interest (a1) unattached.

iv) It will be a biological particle of no interest (a2).

v) It will be a particle pair (or complex) made up of an active bead (b1) and a biological particle of interest (a1) bound together (a1+b1).

vi) It will be a debris particle knocked loose by the agitation of the fluid motion, or particles shedding from the pumps/filters. These particles constitute background noise counts.

Particle types (iii), (iv), (v), and (vi) will NOT have the forward scatter intensity, extinction intensity, transit time, and/or Gaussian fit parameter typical (and expected) of particles of type (i) and (ii).

So the computer is essentially determining in which group any one particle belongs to as it detects them passing though the sensing zone of the flow cell. It can accurately discern types (i) and (ii), but it can not accurately separate types (iii), (iv), (v), and (vi). So there are 3 types of particles of interest to the computer. Type (i), type (ii), and NOT type (i) or type (ii).

Figure 8:
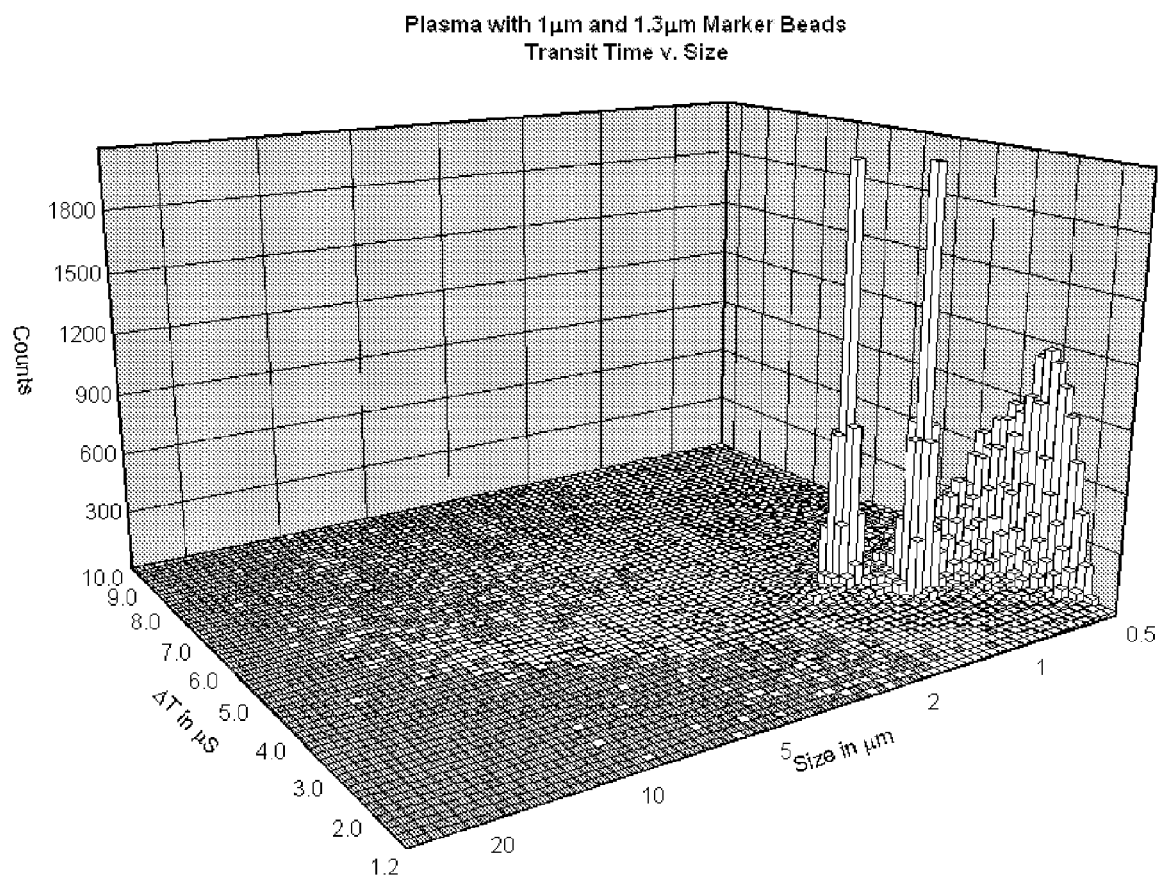
FIG. 8 is a chart showing transit time (µsec) versus particle size (microns) for latex particles with a size of 1.0 and 1.3 microns in a colloidal suspension of biological particles.

The data is stored in a histogram representation. A 3D version of this histogram can be seen in FIG. 8, showing two parameters, Transit time ($\Delta T$) vs Size vs counts. The instrument can be calibrated to indicate particle size for any particular index of refraction (ie. latex calibration), or extinction/scatter intensity can be used directly for the axis/histogram bin labels.

Figure 9:
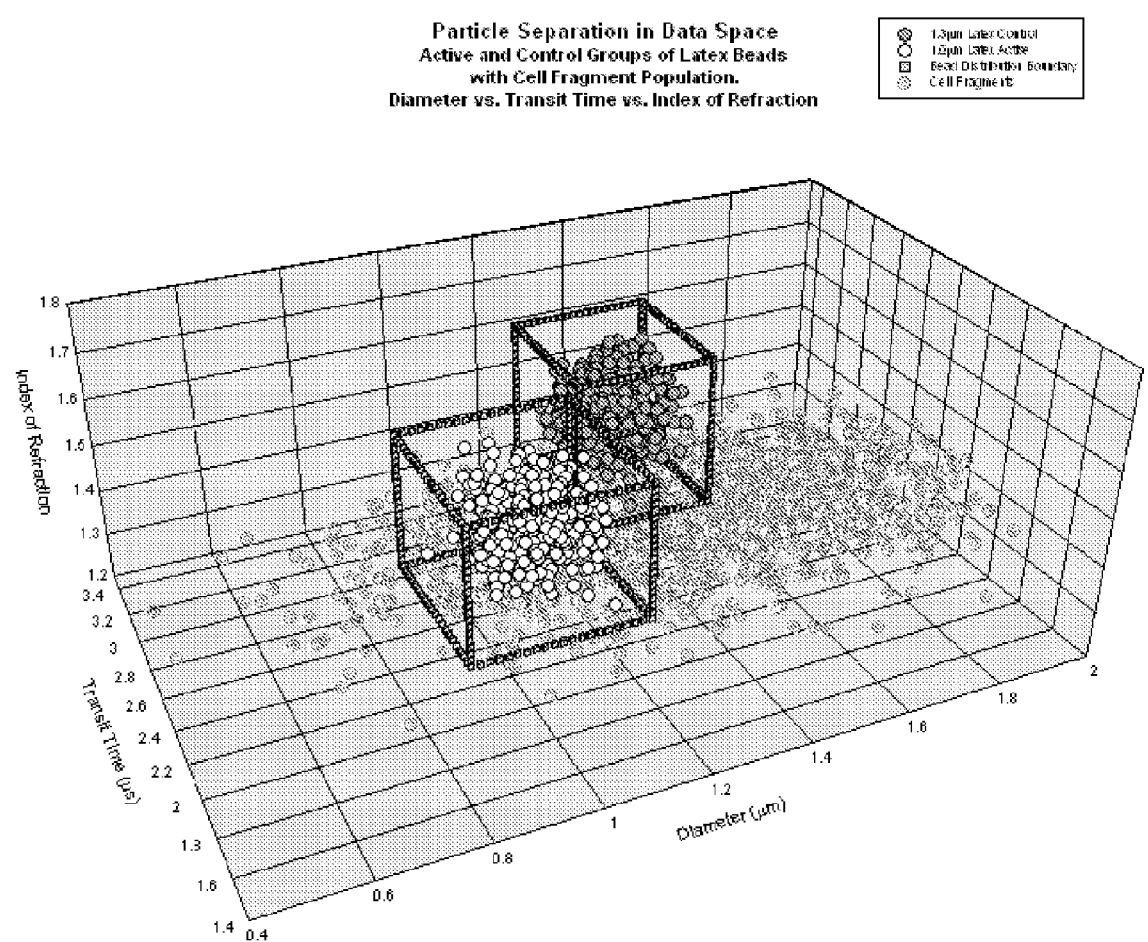
FIG. 9 is a chart showing three populations of particles, in three dimensional space, plotted as a function of index of refraction, diameter (microns) and transit time (µsec).

FIG. 9 provides a representation of active (b1) and marker (b2) beads in data space with biological particles in the background. The bounding boxes delimit the data space volumes that particles of type (i) and (ii) are expected to be measured in.

Each parameter being measured i.e. Extinction Intensity for marker beads, has an upper range value, and a lower range value that is experimentally ascertained during instrument calibration. A value outside that range disqualifies a particle from belonging to that group.

The parameters that are subject to calibration with upper and lower bounds are Scatter Intensity, Extinction Intensity, Transit Time, and Gaussian Fit parameter for marker beads (b2); Scattered Intensity, Extinction Intensity, Transit Time, and Gaussian Fit parameter for active beads (b1).

Analysis

After all of the sample taken from suspension (c) has been processed, and the information has been disseminated into the various histograms by the computer, several conclusion can be reached.

Note: By "All" we mean that the same concentration of beads (beads/mL) that was in the original (unmixed) colloidal suspension is now found in the (mixed) and processed suspension.

Recovery is made to with a certain statistical certainty. i.e. 99% recovered, or to within 1% of what was expected.

1) IF All of the Marker beads (b2) are recovered, THEN no loss has occurred due to transport and processing of the active and marker beads.
2) IF All of the Active beads (b1) are recovered, THEN there was no bindings to Biological Particles of Interest, either because none were present in the biological sample of interest, or the preparation was improperly handled.
3) IF All of the Active (b1) beads are recovered, but Some of the Marker (b2) beads are recovered, THEN there was something wrong with the original colloidal suspension, and the test should be repeated with fresh stock.
4) IF Some of the marker beads (b2) are recovered, THEN something went wrong with the bead transport in the suspension and the final answer the instrument gives has to be adjusted to accommodate for this loss. The answerer may not be a wrong one, but it is certainly suspect.
5) IF Some of the active beads (b1) are recovered, AND All of the marker beads are recovered (b2) THEN the quantity of beads missing from the active group is the number bound to biological particles of interest (a1). This is the important numerical answer the instrument provides. The number per mL of active surface antigens found in the biological sample.
6) IF nothing is recovered, THEN there is a problem with the instrument.
7) IF All of the marker beads (b2) are recovered, AND none of the active beads (b1) are recovered, THEN the biological sample contained a concentration of particles of interest greater than the active bead population, and the test should be repeated with more dilute biological sample. It does however indicate the presence of biological particles of interest and serves to indicate a lower bound of their concentration. i.e. "Biological particles present in Greater than N/mL concentration in the sample." where N/mL is the concentration of the Active (b1) beads in the colloidal suspension (c).

Using the reasoning table above the instrument can now report on the biological sample of interest. Either there was none in the original suspension (all of the active beads were recovered), there was some in the original suspension and the instrument can report numerically on what that concentration was (number per mL), or there was an overabundance of biological material of interest (it consumed all of the active beads), and a further experiment needs to be performed with a more dilute sample to accurately get a concentration figure.

This information can then be reported to the user running the instrument in a screen/paper report, and/or saved in a database of results.

Methods of Identifying Subjects Non-Responsive to Platelet Therapy

Plavix and other drugs are used to bind platelets, and inhibit their ability to cause blood clots. If a patient has blood platelets that do not bind to Plavix or such other drugs, then they will not respond to that particular therapy.

Blood samples of subjects can be screened for the ability of the platelets to bind to one or more active particles, where the active particles are covalently bound to one or more Plavix molecules, or other such drugs. One can isolate blood platelets, and then incubate the platelets with a colloidal suspension of the active beads. In this manner, the surface of the either resting or activated platelet can be mapped or phenotyped to determine the presence or absence of a specific epitope. Congenital absence of glycoptotein IIb/IIIa (gpIIb/IIIa) (Glanzmann's thrombastheina) can be assessed. Further, in normal platelets, gpIIb/IIIa is present on activated platelets and is required for fibrinogen binding in normal platelet aggregation. Pharmocologic agents like Rheopro are administered during cardiac catheterization to block fibrinogen binding and prevent a platelet thrombus from forming during the procedure. To be effective, at least 80% of the gpIIb/IIIa receptors (integrin $\alpha 2b\beta 3$) must be blocked. Adequacy of therapy can be determined by prevention of beads conjugated with an antibody against gpIIb/IIIa to the patient's platelets. In a similar manner, the appearance of platelet activation markers like CD41 or CD62p can be determined in patients who take Plavix or aspirin as treatment for coronary artery disease. If the therapy is adequate, the platelet will not activate and the biomarker will not be present on the platelet surface. Personalized medicine is possible using the techniques described herein, and can be conducted in a rapid, simple and inexpensive manner.

In one embodiment, an optimized of the colloidal suspension of active beads is incubated with a suspension of platelets and a control that does not include platelets. The total number of active beads not bound to platelets in both samples can then be determined, and if the number of active beads in the sample has been reduced relative to the number of active beads in the control, one can deduce that the active beads bound to the platelets. One can also quantify the number of particles of interest in the sample by counting the number of active beads having bound to particles of interest.

In another embodiment, an aliquot of a colloidal suspension including both active beads and marker beads is incubated with an aliquot of a colloidal suspension of platelets. The relative number of active beads to marker beads not bound to platelets in both samples can then be determined, and if the number of active beads has been reduced, one can deduce that the active beads bound to the platelets.

Methods of Detecting Genetic Variants

The present invention can be used to determine the presence or absence of genetic mutations. The methods involve:
  a) extracting genomic DNA from a cell,
  b) mixing the genomic DNA with an active particle, where the active bead is linked to a genetic probe that is complementary to a genetic disease marker, and wherein the quantity of binding particles before the mixing step is known
  c) incubating the host DNA and the active bead for a sufficient time and at a sufficient temperature to allow binding of the host DNA to the genetic probe, if the host DNA includes complementary DNA, and
  d) determining whether the probe hybridized to the marker by counting the number of active beads not bound, and comparing that number to the original number of active beads (i.e., the number of beads in the aliquot of the active beads), or comparing the ratio of active beads to marker beads at the beginning and end of the assay.

If the number of active beads has not changed (or ratio of active beads to marker beads), this is indicative that the sample of genomic DNA did not include the mutation of interest. If the number of active beads changed, where a probe signal was present (because the probe had hybridized to the marker), this might mean that the patient had a specific disease-associated mutation. Conversely, lack of a signal would indicate absence of that mutation.

In one embodiment, the genomic DNA is isolated from white blood cells or other biological particles. Typically, one can obtain genomic DNA from white blood cells using a four-step process, starting from a representative blood sample. The red blood cells are lysed, leaving the white blood cells intact. The white blood cells and their nuclei are lysed and solubilized, for example, in a nuclei lysis solution. If desired, an RNase digestion step can be included. The cellular proteins are then removed by salt precipitation, which precipitates the proteins but leaves the high molecular weight genomic DNA in solution. The genomic DNA is then concentrated and desalted, for example, by isopropanol precipitation.

In one embodiment, the assay determines whether or not a subject has genetic mutations in their cytochrome P450 gene, or mutations related to other mutations that adversely affect drug metabolism enzymes (DMEs). Such genetic mutations are largely known, and include those described in PCT WO 2007/097884.

There are also markers that predict whether a drug will be effective for a select number of therapeutic areas. For example, one can look for mutations such as B2AR (β-adrenergic receptors—important for patients being treated for asthma with Albuterol), ERCC1 (excision repair cross complementing gene 1; may affect DNA repair capabilities), ERCC2 (excision repair cross complementing gene 2; may affect DNA repair capabilities), MDR1 (multidrug resistance gene 1; determines drug absorption in tumor cells), XRCC1 (X-ray repair cross complementing gene 1), VKORC1 (an enzyme involved in vitamin K recycling and the drug target for warfarin) and 5HTT (5-hydroxytryptamine transporter; a.k.a. SLC6A4-determines effectiveness of drugs used to treat depression and other CNS disorders.

DMEs that predict drug toxicity could also be considered efficacy markers since the presence of adverse effects may limit therapeutic efficacy and may require discontinuation of an otherwise effective treatment. Irinotecan (Camptostar) has been approved for the standard therapy of colorectal cancer. Although irinotecan is a promising chemotherapeutic agent, the most common unwanted side effects are bone marrow toxicity leading to abnormal blood counts, in particular leucopenia and ileocolitis. Irinotecan is metabolized to form active SN-38, which is further conjugated and detoxified by UDP-glucuronosyltransferase (UGT) IA1 enzyme. Genetic polymorphisms of the UGT1A1 would affect an inter-individual variation of the toxicity by irinotecan via the alternation of bioavailability of SN-38. Determination of the UGT1A1 genotypes can be clinically useful for predicting severe toxicity by irinotecan in cancer patients.

Patients suffering from various genetic disorders can also be identified using the genomic screening techniques described herein. One example of a disorder that can be identified through genomic screening is Cystic Fibrosis. More than 1000 mutations of the CFTR gene are listed in the Cystic Fibrosis Mutation Data Base. Mutations that can be identified include 1898+IG>A, I148T, 2184delA5 1078delT, 394delTT, S1235R, and combinations of the IVSB polyT tract variant alleles 5T, 7T, and 9T.

Another mutation that can be confirmed via genomic screening is a MTHFR deficiency. MTHFR (Methylenetetrahydrofolate reductase) is important in folate metabolism, and mutations in this gene may lead to increased concentrations of homocysteine. Increased concentrations of homocysteine are associated with severe neurologic impairment. One thermolabile variant, 677C>T, does not appear to be associated with neurologic symptoms, but may be associated with an increased risk for vascular disease, and has an estimated frequency of up to 24% depending on the population. Clinical testing for MTHFR 677C>T is widespread as part of a cardiovascular risk panel.

Another type of mutation that can be identified is present in the HFE (hemochromatosis) gene, with a frequency believed to be in excess of 10% in the Caucasian population. These mutations are associated with hereditary hemochromatosis, and include mutations in C282Y, C282Y/H63D, H63D, and S65C, with heterozygotes such as H63D/S65C.

Other mutations are associated with a risk for thrombosis. These genes are typically associated with coagulation factor V (F5) and prothrombin (F2), and mutations such as FVL and the prothrombin polymorphism 20210G>A.

Defects in the connexin 26 gene (GJB2) are thought to be responsible for ~50% of all nonsyndromic autosomal recessive deafness, and 70% of the currently identified connexin 26 mutations are of the type carried by DUK1 9946. Since the link between connexin 26 and deafness was established in the 1990s, a demand for clinical testing for mutations in the connexin 26 gene has developed.

Deletions in the α-globin gene cluster are common in certain populations and cause α-thalassemia with various degrees of severity, depending on the type of deletion. Several different deletions have been identified in the α-globin gene cluster, which deletions can be detected using the methods described herein. Examples include type 1 deletions (both α-globin genes deleted; 1 heterozygous SEA deletion and 1 heterozygous FIL deletion), and type 2 deletions (1 gene deleted; heterozygous).

There are also various known point mutations in the β-hemoglobin (HBB) gene: the Hb S mutation, which is responsible for sickle cell disease, and the Hb C mutation, which is associated with chronic hemolytic anemia. The Hb S and Hb C mutations occur in the same codon. Hb S leads to the substitution of valine for glutamic acid, whereas Hb C leads to the substitution of lysine. The presence of both mutations in a compound heterozygous state causes Hb SC disease, which has characteristics of both sickle cell and Hb C disease. Because the 2 mutations occur in such close proximity to one another, they are often tested for simultaneously.

The present invention will be better understood with reference to the following non-limiting examples.

Example 1

Aspirin Assay

In this assay 100 microliters of resting platelet rich plasma obtained from a patient who is being treated with aspirin is incubated with the colloidal suspension of the active beads and non-active beads so that complex formation, if any, can occur. The incubation mixture is then counted for the presence of complex formation between the active beads and the resting platelets as well as for any depletion in the active bead population. No complex formation and no significant active bead population depletion confirm resting platelets.

This result is followed by an identical test except the platelets have been activated with arachidonic acid. If no complex formation is noted and no significant active bead population depletion is noted, the patient's platelets were adequately inhibited by aspirin and the patient is adequately treated. Any evidence for platelet activation would indicate that the patient is not adequately treated. Up to 25% of patients taking aspirin do not respond and are thus not adequately treated.

Example 2

Plavix (Clopidogrel) Assay

In this assay 100 microliters of resting platelet rich plasma obtained from a patient who is being treated with Plavix is incubated with the colloidal suspension of the active beads and non-active beads so that complex formation, if any, can occur. The incubation mixture is then counted for the presence of complex formation between the active beads and the resting platelets as well as for any depletion in the active bead population. No complex formation and no significant active bead population depletion confirm resting platelets.

This result is followed by an identical test except the platelets have been activated with ADP adenosine diphosphate, that activate a receptor on the platelet surface, P2Y12. Plavix inhibits this receptor and prevents platelet activation. Up to 30% of patients taking Plavix do not respond to this drug. If no complex formation is noted and no significant active bead population depletion is noted, the patient's platelets were adequately inhibited by Plavix and the patient is adequately treated. Any evidence for platelet activation would indicate that the patient is not adequately treated.

Example 3

Microbial Infection Using a *Streptococcal Empyema* Assay

Five to 10 mL of pleural fluid is placed in a centrifuge tube and spun to sediment any particulate material. The pellet is resuspended and incubated with the colloidal suspension containing active beads against common pathogens, in this case streptococcus pneumonia. After complex formation between the active beads and the bacteria have formed, the incubated solution is placed in the device and examined for the presence of complex formation and depletion of the active bead population that would indicate the presence of streptococcal pneumonia.

Example 4

Assay to Identify Circulating Tumor Cells

The detection of circulating tumor cells is becoming an important finding that indicates the presence of residual cancer and prompts re-treatment. Most means to detect minimal residual disease is expensive, complicated and time-consuming.

Two strategies are possible in this assay. First case: In this assay 7.5 mL to 10 mL of plasma would be obtained and mixed with active beads. In this case the beads would be magnetic beads. After complex formation a magnetic field would be applied and any un-bound particles washed away. The magnetic field would then be relaxed and the beads counted.

In the second case: non-magnetic active beads would be complexed to the tumor cells via a specific antibody against a characteristic tumor epitope. The sample would then be counted directly.

Example 5

DNA Probe: Genomic DNA is Extracted from Sample Cells

DNA fragments are then incubated with active beads that have the probe DNA chemically linked to them. In this case the active beads size is small in the range of 0.3 microns to 0.5 microns. After incubation, the sample is placed in the device and examined. Depletion of the active bead population and the appearance of a bead complex will indicate identification of a specific sequence of genomic DNA.

In a like manner polymerase chain reaction (PCR) products could be hybridized with a probe that has been chemically linked to a bead (gold, glass, other other) and then counted. The advantage is that slab gel electrophoresis would not have to be run. The PCR cycle count could be drastically reduce thus saving time, money, the complexity of slab gel electrophoresis.

Example 6

Representative Analytical Device

Sample Fluid Transport.

A representative device is shown in FIG. 11. A colloidal suspension containing particles of interest, particles of no interest, marker beads, active beads, and possibly keying beads (the sample) is introduced by the operator of the instrument to an inlet tube (See FIG. 10), via means of a controlling computer intake valve (10), which energizes the valve, causing it to open and allow fluid to pass through it, and a syringe pump (20) is activated in such a way as to cause suction at the inlet tube (a lowering of pressure).

By means of the pressure difference between the atmosphere and the lower pressure inside the inlet tube, the sample is introduced into the inlet tube, and travels into the device (shown in FIG. 11) through intake valve (10) and into the sample storage loop (30). Syringe pump (20) stops its motion after a precise volume has been transferred from the sample container, and into the instrument, (mostly into the storage tube). No sample is allowed to be introduced to the syringe. This is accomplished by precise volumetric pumping of syringe pump (20).

Intake Valve (10) is de-energized, thereby blocking the fluid pathway, while simultaneously syringe pump (20) is stopped so that all fluid motion stops with the instrument. A further valve (40) is energized causing it to open its fluid path and allow fluid to flow through it while the direction of motion of the syringe pump (20) is reversed. Syringe pump (20) is activated in such a way as to push fluid out of itself, thereby forcing the fluid in the storage loop to be transferred through valve (40) and into the hydrodynamic focus chamber (the pre-cell chamber where hydrodynamic focus is achieved for the particles to be measured is shown in FIG. 10) sample inlet port. Metered pump (50) is energized causing fluid to be drawn from the water (or other diluent fluid connected to the machine) reservoir, through particulate filter (60) and into the hydrodynamic focus chambers sheath inlet port. Data is gathered during the time that both pumps are activated and are pushing fluid into the hydrodynamic focus chamber and subsequently into the cell (70). The syringe pump (20), and metered pump (50) stop their motion when all of the sample fluid has been pushed into the hydrodynamic focus chamber and the data from the sample has been collected. The valve (40) is then closed.

Fluid sensors (80, 90, and 100) can also be present, for example, near where the intake of water occurs, near where introduction of cleaning agents occurs, and where intake of the sample occurs, respectively.

Hydrodynamic Focus.

During the data gathering phase sheath fluid is pumped into the hydrodynamic focus (pre-cell chamber (3) in FIG. 10) by metered pump (P2 in FIG. 11) via a sheath inlet port, while sample is pumped out of the storage loop and into the (hydrodynamic focus) pre-cell chamber (3) by syringe pump (P1 in FIG. 11) (See FIGS. 10 and 11). In the chamber, and by means of the physical geometry of the chamber (i.e., the chamber is tapered, so that the outlet side is reduced in diameter from the inlet), the sheath fluid (provided via sheath tube (2)) surrounds the sample fluid (provided via sample feed tube (1) to the bottom of the feed tube (4), and both are transported out of the chamber and into the flow cell. The tapered geometry of the chamber and the pressure introduced into the chamber by both pumps causes both fluids to accelerate in motion, and to be reduced in diameter as they travel out the exit port (on the bottom in FIG. 10 (5)). The effect of this is that the sample stream is now much thinner than it was when it was introduced into the chamber, and is kept away from the walls by means of the sheath fluid. Due to the pumping action of pumps (P1) and (P2), the sheath fluid and sample fluid travel unmixed out of the hydrodynamic focus chamber and into the optical flow cell.

The Flow Cell.

The optical flow cell is made of transparent glass or quartz for the wavelengths of light that are emanating from the laser, and contains within it a hollow flow channel in which the sheath fluid and sample fluid flow. In the optical flow cell, light from the laser traveling perpendicular to the direction of travel of the fluid, interacts with the particles in the fluid stream at the sensing zone, in such a way as to cause some light to be absorbed some to be scattered in all directions. Every particle that passes through the sensing zone does this, even though not all are seen by the detectors as they may not interact with the light strongly enough to be detected.

Sensing Zone.

A laser emits a cylinder of light in a coherent fashion, and oscillating at a very narrow range of wavelengths, and said light travels in a direction toward the flow cell (see FIG. 12). The cylinder of light emanating from the laser is shaped into a thin ribbon of light by means of a cylindrical lens positioned in the path between the cell and the laser at such a distance so that the focal point of the cylindrical lens is coincidental with the point in space that the sample fluid passes through. The light impinges upon the sample flow in the flow cell and is perpendicular to it. This practice of focusing the beam on to the flow stream is well known to those skilled in the art. The volume formed by the intersection of the thin line of light formed by focusing in one dimension the cylinder of light emanating from the laser, and the cylinder of sample fluid sounded by the sheath fluid, is known as the sensing zone. It is from this sensing zone that all light that is scattered and otherwise absorbed by the particles is detected by the systems two detectors.

Extinction Detector.

When a particle enters the sensing zone, light from the laser interacts with it, and some of the light is absorbed by the particle, and some is scattered. Most of the light from the laser passes through the cell, interacting with it in a trivial way and in a fashion not detectable by the scatter and extinction detectors. The light that is absorbed by the particle and the light that is scattered away from the extinction detector creates temporarily, a diminution in the intensity of the laser beam as sensed by the extinction detector. It is this intensity diminution that the extinction detector sees as a negative going pulse (as light is removed from the beam), and it is this effect that causes the extinction detector to detect the particle in the sensing zone. Light makes it to the extinction detector by means of a small minor placed after the exit of light from the flow cell, and before the first scatter collection lens, whose purpose is to redirect the light away from the scatter detector and onto the sensing area of the extinction detector.

Scatter Detector.

While a particle is in the sensing zone, some of the light that interacts with it is absorbed by the particle and some of the interacting light is scattered in all directions. The portion of light that is scattered in the direction of the collection lenses is called the forward scattered light. Some of the forward scattered light has its direction of travel changed by the scatter collection lenses, and steered toward the scatter detector. The scatter detector converts this energy into a current that is then processed by the detector electronics. This increase in intensity of light impinging upon the scatter detector when a particle is in the sensing zone, is the effect that causes the scatter detector to sense a particle.

Signal Generation.

Both detectors produce a current proportional to the amount of light that is impinging upon them. By means of a trans-impedance amplifier and a feedback resistor, this current is converted to a voltage for further processing by the data collection subsystem. In the case of the scatter detector, the current is low when there is no particle in the sensing zone, and rises to a maximum value, representative of the amount of light scattered by the current particle in the sensing zone, and back (down) again to its previous value, thus forming a positive going current pulse. In the case of the extinction detector, the current is high where there is no particle in the sensing zone, and diminishes to a minimum value, representative of the amount of light scattered and absorbed by the current particle in the sensing zone, and back (up) again to its previous value, thus forming a negative going current pulse. (See FIG. 12.)

Data Collection.

The voltage pulses produced by the trans-impedance amplifiers are digitized by an A/D converter and the digital representation of those intensities is provided into the computer for further processing.

Data Processing

In one embodiment of the apparatus described herein, the apparatus includes a total extinction detector and a forward scatter detector. As particles flow in the stream passing through the instrument sensing zone, two signal streams are generated, one in the extinction detector, and one in the scatter detector. The signal stream can then be digitized using known analog to digital (A/D) means, and the information can be entered automatically into a computer.

In one embodiment, this information is then input into a software program running in the computer, which program computes a series of information about this event (i.e., the information on the particles as they pass through the sensing zone. The information includes one or more of the following:

TIME of ARRIVAL (computer clock time at the beginning of pulse)—(beginning of pulse is defined as the time the signal voltage level has registered above a minimum threshold value); INTENSITY (the point of maximum signal intensity within that pulse);

TRANSIT TIME (as measured at the base (just above baseline) or the width in time, at the half height of the pulse);

SHAPE PARAMETER (as a fraction of fit to a mathematical Gaussian pulse 1=perfect fit).

This information can be captured for both detectors, so a table of acquisition values can be built up containing up to 7 values for each event. These values include:

1) Particle Arrival time
2) Extinction Intensity
3) Extinction Transit Time
4) Extinction Fit Parameter
5) Forward Scatter Intensity
6) Forward Scatter Transit Time
7) Forward Scatter Fit Parameter This information can be tabulated, for example, as follows:

| Arrival Time | Ext. Intensity | Ext. ΔT | Ext. Fit | FS Intensity | FS ΔT | FS Fit |
|---|---|---|---|---|---|---|
| 120 (μs) | 3254 (mV) | 6.4 (μs) | 0.9672 | 2106 (mV) | 3.7 (μs) | 0.9511 |
| 127 (μs) | 1109 (mV) | 2.1 (μs) | 0.8743 | 908 (mV) | 1.6 (μs) | 0.8936 |
| 144 (μs) | 2788 (mV) | 8.7 (μs) | 0.5628 | 1185 (mV) | 6.7 (μs) | 0.6129 |
| 152 (μs) | 3101 (mV) | 6.0 (μs) | 0.9880 | 2035 (mV) | 3.5 (μs) | 0.9663 |

. . . and so on . . .

In one embodiment, the instrument includes a library table of values whose entries form a set of inclusion/exclusion criteria for the particles used in this particular assay being conducted. The library can be used to determine whether a particular particle falls inside or outside a bounding box. Whether or not a particle falls inside or outside a "bounding box" determines whether it is an active or marker particle (in which case, they would typically be within the bounding box) or a complex of the active particle and a particle of interest (which would typically fall outside the bounding box).

The library of information can be stored, for example, in a data file or in permanent storage, using storage techniques known to those of skill in the art. A library ideally includes information on a plurality of particles, for a plurality of criteria (i.e., particle size, index of refraction, density, fit to Gaussian curve, and the like). Ideally, the library includes information one three or more, preferably ten or more, and more preferably, one hundred or more types of particles, and at least two, and preferably three or more criteria for each of the particles.

A "Bounding box" is defined herein as the location in data space of a hypothetical hypercube (in one embodiment, one having six dimensions, or a 6-cube)—where the library table of values provides the bounding surfaces of the hypercube.

The particular type of assay being conducted during a given run, and the subsequent table to use for the inclusion/exclusion criteria, can be provided by the operator as part of the set-up phase of the given run, or that information could have come from a keying assay containing keying beads.

If a keying assay (an assay that contains keying beads) is used, then the system can pick the inclusion/exclusion criteria from a library table of criteria that is prestored in the machine, once it determines the code value of the key from the keying beads.

Keys can be coded in the data space of a single detector (most likely the extinction detector). In other words, the instrument looks at the histogram (the totality of counts acquired from this detector summed for each voltage channel into a histogram) of Extinction Intensity (X Axis) vs. Counts (Y Axis), and if it finds the presence of keying beads at a particular intensity (and in statistically significant quantities) (within a range of intensities that it Never expects to find biological particles, and in a range that it does expect to find keying beads), then it identifies the key code for this assay, and uses the proper entries in the table.

If the particle falls within a data hypercube for this assay, then it is counted as such. If it falls outside the data hypercube it is counted in a separate counter (a variable in the software is incremented by one). One or more data hypercubes may be used in a single assay.

Figure 13:
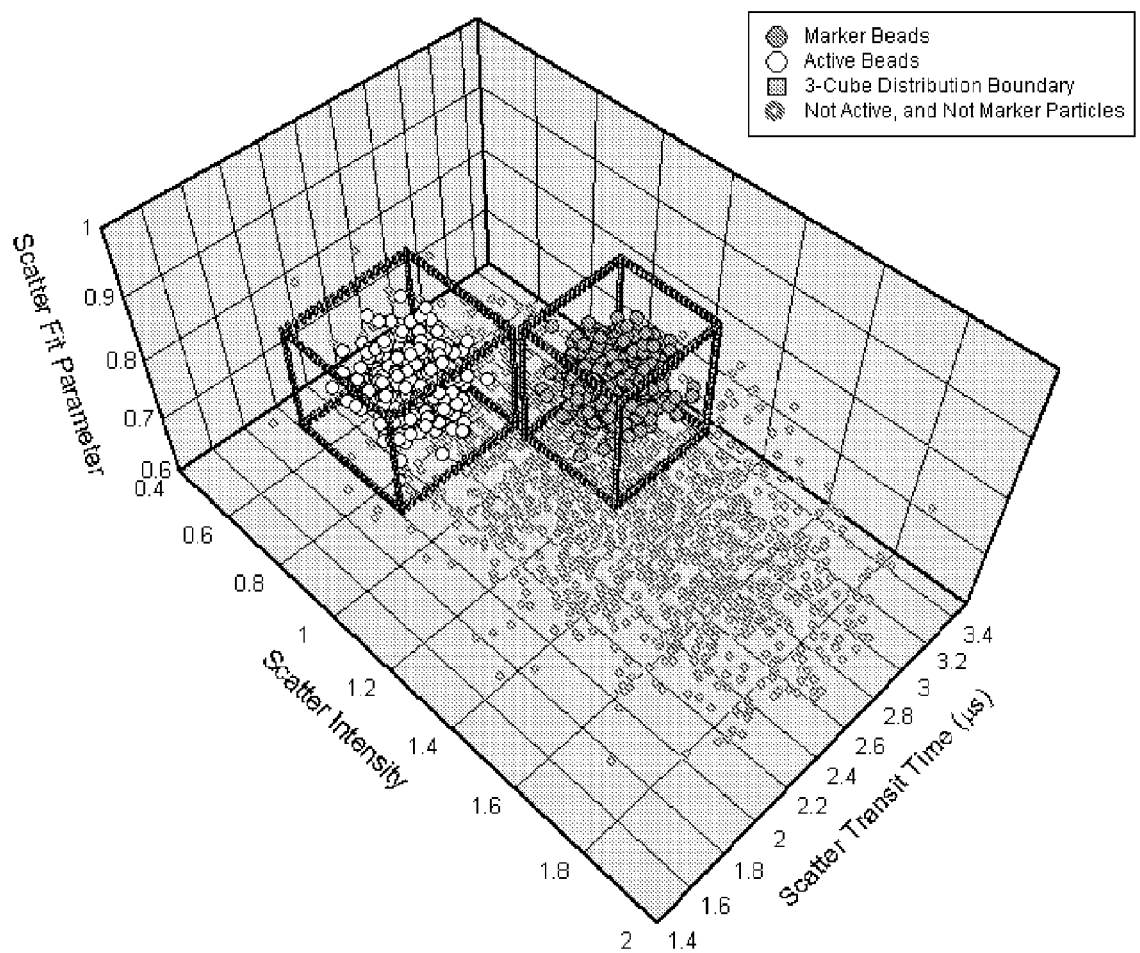
FIG. 13 is a chart showing the population distribution differential in terms of number and size (μm) or particles.

Additionally, individual channels of data may be histogrammed or otherwise tabulated for presentation to the user in numeric or graphical form. A representative table is shown in the following table, as well as in FIG. 13.

| Diameter | Count | Cum # >= Dia. | Num % | Area % | Vol % | Num % <= Dia. | Vol % <= Dia. |
|---|---|---|---|---|---|---|---|
| 0.513 | 567 | 23176 | 2.446 | 0.114 | 0.003 | 2.446 | 0.003 |
| 0.541 | 1329 | 22609 | 5.734 | 0.297 | 0.008 | 8.181 | 0.011 |
| 0.570 | 1644 | 21280 | 7.094 | 0.407 | 0.011 | 15.274 | 0.022 |
| 0.600 | 1038 | 19636 | 4.479 | 0.286 | 0.008 | 19.753 | 0.031 |
| 0.632 | 333 | 18598 | 1.437 | 0.102 | 0.003 | 21.190 | 0.034 |
| 0.666 | 125 | 18265 | 0.539 | 0.042 | 0.001 | 21.729 | 0.035 |
| 0.702 | 76 | 18140 | 0.328 | 0.029 | 0.001 | 22.057 | 0.036 |
| 0.740 | 51 | 18064 | 0.220 | 0.021 | 0.001 | 22.277 | 0.037 |

In one embodiment, there is one set of defining values (12 entries) in the library table of values for each hypercube surrounding each of the following particles. Each active bead in the assay has a table of 12 values, and each marker bead has a table of 12 values, and all keying beads have a table of 6 values (because keying beads most likely fall outside the range of the scatter detector).

The 12 table entries for active and marker beads are namely—in no particular order:
vii) Upper limit Transit Time for Extinction,
viii) Lower limit Transit Time for Extinction,
ix) Upper limit Transit Time for Scattering,
x) Lower limit Transit Time for Scattering,
xi) Upper limit Intensity for Extinction,
xii) Lower limit Intensity for Extinction,
xiii) Upper limit Intensity for Scattering,
xiv) Lower limit Intensity for Scattering,
xv) Upper limit Gaussian Fit Parameter Extinction,
xvi) Lower limit Gaussian Fit Parameter Extinction,
xvii) Upper limit Gaussian Fit Parameter Scattering,
xviii) Lower limit Gaussian Fit Parameter Scattering.

The 6 table entries for keying beads are namely—in no particular order:
a) Upper limit Transit Time for Extinction,
b) Lower limit Transit Time for Extinction,
c) Upper limit Intensity for Extinction,
d) Lower limit Intensity for Extinction,
e) Upper limit Gaussian Fit Parameter Extinction,
f) Lower limit Gaussian Fit Parameter Extinction, Numerical values for the location of the bounding surfaces of the hypercubes surrounding each particle type can be derived from experimental data to which a maximum and minimum value has been determined (for example, by adding and subtracting a constant from the mean, in one case, where the constant is chosen so as to include greater than 95, preferably greater than 98, and more preferably greater than 99% of the population of beads, or such other percentage deemed acceptable to the manufacturer).

The accuracy of the instrument can periodically be checked against NIST traceable reference beads of known diameter and makeup, and a table of intensity vs. mean bead diameter can be saved for each instrument and for each bead size thus tested. This is known as instrument calibration, and the calibration tables generated can be stored internally to the instrument (or associated computer), in a file on the hard drive or in EEPROM (Electrically Erasable Programmable Read-Only Memory).

In other words, if a reference bead of a known diameter is measured by one instrument, and a particular average intensity value is established for this bead in this instrument, that information can then be stored in that instrument's memory (or memory on a computer operatively linked to the instrument). Another similar instrument may measure a bead population of identical size, but arrive at a slightly different value of mean intensity. This table is known as the calibration table for the instrument, and the values only pertain to that particular instrument. Thus, many instruments can measure beads from different assays, and they will correctly position and qualify the beads.

At the end of a particular run (where a run is defined as the data collection activity of the instrument) each particle has been counted as belonging to one of several groups. These groups include one or more, and preferably two or more, of the following:
one or more of the groups of active beads;
one or more groups of marker beads;
one or more groups of keying beads;
and one or more groups enumerating everything else not counted in one of the active, marker, or keying groups.

The members of the last group typically include biological particles of interest that are unbound, biological particles of no interest, and biological particles of interest attached to active beads.

If all (as used herein, 'all' means 'all' or 'most'—within a statistical acceptable loss, for example, a 97% recovery rate is acceptable) of the particles in the marker group have been counted inside their expected bounding hypercube, then the run is deemed a success, as all marker beads have been accounted for.

Figure 14:
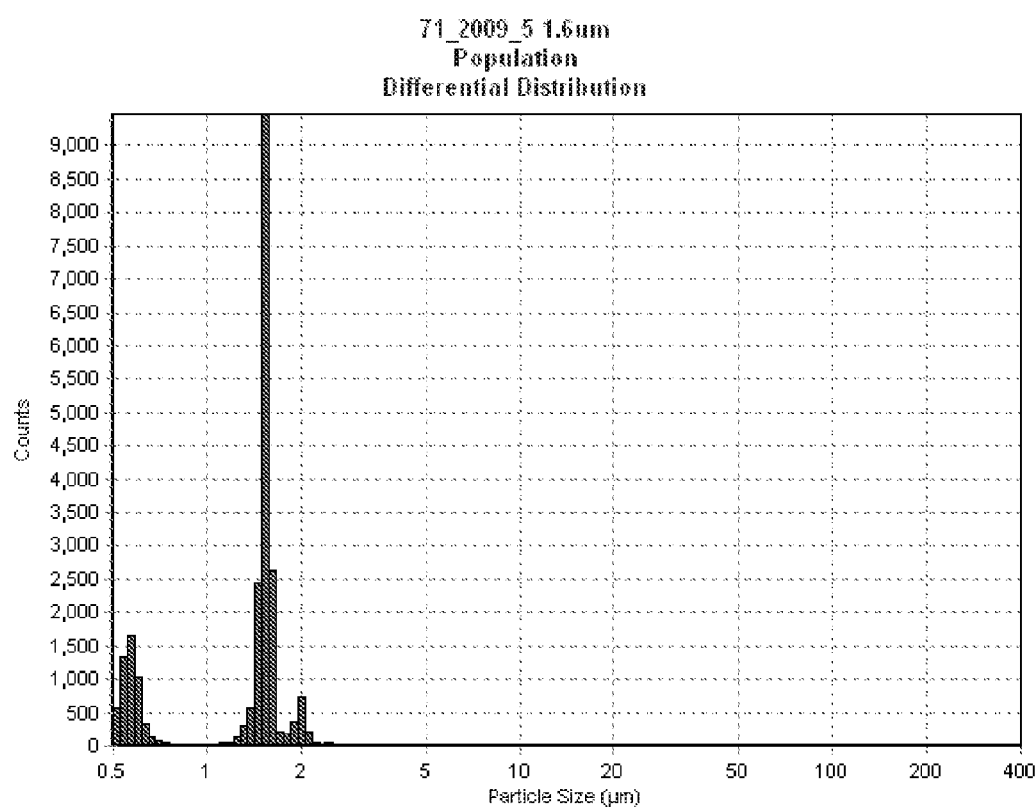
FIG. 14 is a chart showing data space separation in three dimensions, measured in terms of scatter fit parameter, scatter intensity, and scatter transit time (μs).

As shown in FIG. 14, a 3-Dimensional representation, using simulated data, illustrating the process is shown, using only a subset of the collected parameters as an example.

Once it is established that a particular run was a success, one can then look at the active beads recovered (counted to be inside) their bounding hypercube. When one looks at the active group, one seeks to identify how many beads were lost (found outside the hypercube) as defined for them by the assay parameters, and, by inference, how many bound to particles of interest. This can be accomplished by taking the number of beads expected to be found inside the respective hypercube (from assay parameters) and subtracting from that number the count of beads that was actually measured to be inside the hypercube. The difference is the measure of the quantity of active beads that bound to particles of interest, and, as a result, were removed from the inside the hypercube count. This is the important number the instrument reports to the user.

There are three possible outcomes for a single group of active particles within one assay:

1) No Active bead was removed from the data hypercube and all were recovered. The concussion to be reached from this is a) there was no particle of interest present in the original colloidal suspension being tested, b) there may have been something wrong with the sample preparation by the user (i.e. not enough time allowed for chemical equilibrium to be reached, or improper mixing, etc.)

2) Some of the active beads are removed from their hypercube data space, and the quantity missing represents the quantity of particles of interest present in the original colloidal suspension. This is reported by the instrument as a number per unit volume (i.e. #/mL) this is the important number forming the answer the user is looking for.

3) All of the Active beads have been removed from their data hypercube. The conclusion to be reached from this is that there were more particles of interest in the original colloidal suspension then were active beads capable of binding to them. So, while the instrument can report that particles of interest do exist in the original colloidal suspension, it can not quantify them, except for being able to give a lower-bound figure (there are at least N #/mL particles of interest in the colloidal suspension). The user at this point may wish to repeat the run with a less concentrated (more dilute) colloidal suspension.

If the run is deemed not a success, then this can be reported to the user. One example of an unsuccessful run is one where there has been some loss of the marker beads (i.e. less than 95% of the expected marker beads were counted during the run). The instrument can still give an answer to the user by rationing the count of active beads missing to the fraction of marker beads that went missing. However, this might be a suspect answer, or at least one that should not be relied upon with as much confidence as one achieved by a successful run (i.e., one where all or most, for example, greater than 95% of the marker beads were recovered.)

It is possible to perform this kind of test in any order of dimensions for the hypercube, depending on the quantity of data channels you have. For instance, if one has only 1 detector (for example, a scatter detector), one can use a 3-dimensional space cube (3-cube) (see illustration above to essentially do the same test. That is, one can qualify beads as being inside or outside the pre-defined volume. Alternatively, if one has three data channels, providing four pieces of information for each channel, then you could theoretically use a 12-cube hypercube to determine whether particles are included or excluded.

Flushing.

In addition to processing colloidal suspensions for the purpose of identifying particles of interest within the suspension, the instrument as a matter of practice requires internal cleaning of those components exposed to a sample in order to prevent contamination of the next sample. This internal cleaning is accomplished by means of a flushing cycle. During a flushing cycle the instrument purges all of its fluid lines of any sample contained therein by means of introducing filtered water (or any other clean transport fluid) in all the lines, under pressure and high velocity. The high velocity being instrumental in removing any particle attached to the inner surface of the wetted component parts. The pumps in addition to transporting the sample fluid during a run, serve a double duty of introducing clean fluid into the component parts of the system during a flush cycle.

Additionally the introduction of sterilizing agents and cleaning agents is periodically required in order to minimize the possibility of a biologically hazardous environment. These agents are introduced into the system by means of the syringe pump, as it can precisely dispense from an external container all such agents, and distribute them throughout the systems wetted components.

All documents cited above are hereby incorporated in their entirety by reference. From the foregoing, it will be obvious to those skilled in the art that various modifications in these methods and compositions can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore intended to be embraced therein. All documents referred to herein are hereby incorporated by reference.

The invention claimed is:

1. A device for characterizing particles present in a colloidal suspension, comprising:
   a) a flow cell,
   b) a forward scattering detector,
   c) a total scatter detector,
   d) a light-generating element capable of generating a plane of light,
   e) collection optics for the scatter detector which allow the user to collect information on a predefined set of forward angles,
   f) a fluid transporting element for transporting fluid through the flow cell.

2. The device of claim 1, further comprising an element for producing hydrodynamic focus of a sample fluid, wherein the element for producing hydrodynamic focus is disposed between the fluid transporting element and the flow cell.

3. The device of claim 2, wherein the element for producing hydrodynamic focus comprises a sample feed tube and a sheath feed tube.

4. The device of claim 1, further comprising an element for calculating one or more values selected from the group consisting of index of refraction, particle transit time, pulse fit parameter, and particle size, wherein these values are calculated based on information related to forward scatter and total scatter of light interacting with particles flowing through the device.

5. The device of claim 1, wherein the light-generating element comprises a laser and a lens, wherein the lens provides a planar light output.

6. The device of claim 5, wherein the lens is a cylindrical lens.

7. The device of claim 1, wherein the fluid transport element is a pump.

8. The device of claim 7, wherein the pump is a syringe pump.

9. The device of claim 3, further comprising a second fluid transport pump for transporting sheath fluid to the sheath feed tube.

10. The device of claim 9, wherein the second fluid transport pump is a metered dispense pump.

11. The device of claim 1, further comprising a library of information related to one or more values selected from the group consisting of index of refraction, particle transit time, pulse fit parameter, and particle size.

12. The device of claim 1, wherein the detector is not a PMT detector.

13. The device of claim 1, wherein the neither forward scattering detector nor the extinction or total scatter detector is a PMT (photomultiplier tube) or APD (avalanche photodiode) detector.

14. The device of claim 1, wherein one or more of the forward scattering detector and the extinction or total scatter detector is a silicon detector.

15. A method of identifying the presence or absence of one or more biological particles of interest, comprising:
   a) obtaining a first sample which comprises at least two types of particles, at least one of which includes a means of attachment to a biological particle of interest, and at least one of which does not include a means of attachment to a biological particle of interest, wherein the at least two types of particles are in a fixed relative predetermined ratio,
   b) obtaining a second sample which may or may not include a biological particle of interest,
   c) introducing an aliquot of the first sample into the second sample, introducing an aliquot of the second sample into the first sample, or introducing aliquots of the first and second samples into a container, which container may or may not include an additional fluid before the aliquots are added to it,
   d) allowing the particles in the first and second sample to interact at a temperature, and for a time, known to be conducive for a biological particle of interest in the second sample, if present, to bind to the particle in the first sample that includes a means for attaching to the biological particle of interest,
   e) passing the resulting mixture through a device of claim 1 and generating information that comprises the number per unit volume of the at least two types of particles in the first sample that have not bound to a biological particle of interest,
   wherein if the number of particles from the first sample that have not bound to a biological particle of interest per unit volume in step e) is lower than the original number of particles per unit volume, this is indicative of the presence of one or more biological particles of interest in the second sample.

16. The method of claim 15, wherein the method is used to identify subjects non-responsive to platelet therapy, the biological particle of interest is a blood platelet, and the active particles are covalently bound to one or more Plavix molecules, or other such drugs that function in vivo by binding to platelets.

17. The method of claim 15, wherein the biological particle of interest is mammalian genomic DNA with a mutation of interest, and wherein the active particle is covalently linked to a primer or probe that selectively binds to genomic DNA comprising the mutation of interest.

18. The method of claim 17, wherein:
   a) the genomic DNA is extracted from a cell, the genomic DNA is mixed with an active particle linked to a genetic probe that is complementary to a genetic disease marker, and wherein the quantity of active particles before the mixing step is known,
   b) the genomic DNA and the active particle is incubated for a sufficient time and at a sufficient temperature to allow binding of the host DNA to the genetic probe, if the host DNA includes complementary DNA, and
   c) determining whether the probe hybridized to the active particle by counting the number of active particles not bound, and comparing that number to the original number of active particles, or comparing the ratio of active particles to marker particles at the beginning and end of the assay.

19. The method of claim 18, wherein the genomic DNA is isolated from white blood cells.

20. The method of claim 15, wherein the biological particle of interest is a bacteria, and the active beads contain moieties which form a complex with the bacteria.

21. The method of claim 20, wherein the bacteria is *Streptococcus pneumonia*.

22. The method of claim 15, wherein the biological particle of interest is a circulating tumor cell.

23. The method of claim 22, wherein the active particle is complexed to the tumor cells via a specific antibody against a characteristic tumor epitope.

* * * * *